(12) United States Patent
Strother et al.

(10) Patent No.: US 7,239,918 B2
(45) Date of Patent: Jul. 3, 2007

(54) IMPLANTABLE PULSE GENERATOR FOR PROVIDING FUNCTIONAL AND/OR THERAPEUTIC STIMULATION OF MUSCLES AND/OR NERVES AND/OR CENTRAL NERVOUS SYSTEM TISSUE

(75) Inventors: Robert B. Strother, Willoughby Hills, OH (US); Joseph J. Mrva, Euclid, OH (US); Geoffrey B. Thrope, Shaker Heights, OH (US)

(73) Assignee: NDI Medical Inc., Cleveland, OH (US)

( * ) Notice: Subject to any disclaimer, the term of this patent is extended or adjusted under 35 U.S.C. 154(b) by 0 days.

(21) Appl. No.: 11/150,418

(22) Filed: Jun. 10, 2005

(65) Prior Publication Data

US 2005/0277999 A1    Dec. 15, 2005

Related U.S. Application Data

(60) Provisional application No. 60/680,598, filed on May 13, 2005, provisional application No. 60/599,193, filed on Aug. 5, 2004, provisional application No. 60/578,742, filed on Jun. 10, 2004.

(51) Int. Cl.
*A61N 1/18* (2006.01)

(52) U.S. Cl. ............................ 607/40; 607/41; 607/45; 607/46; 607/48

(58) Field of Classification Search .................. 607/48, 607/45–46, 40–41
See application file for complete search history.

(56) References Cited

U.S. PATENT DOCUMENTS

| | | | |
|---|---|---|---|
| 4,232,679 A | 11/1980 | Schulman | |
| 5,113,869 A | 5/1992 | Nappholz et al. | |
| 5,154,172 A | 10/1992 | Terry, Jr. et al. | |
| 5,215,086 A | 6/1993 | Terry, Jr. et al. | |
| 5,222,494 A | 6/1993 | Baker, Jr. | |
| 5,330,515 A | 7/1994 | Rutecki et al. | |
| 5,344,439 A | 9/1994 | Otten | |
| 5,411,537 A | 5/1995 | Munshi et al. | |
| 5,540,730 A * | 7/1996 | Terry et al. ................... 607/40 |
| 5,588,960 A | 12/1996 | Edwards et al. | |

(Continued)

OTHER PUBLICATIONS

U.S. Appl. No. 60/486,573, filed Jul. 2003, Loeb et al.

(Continued)

*Primary Examiner*—Carl Layno
*Assistant Examiner*—Shevon Johnson
(74) *Attorney, Agent, or Firm*—Ryan, Kromholz & Manion, S.C.

(57) ABSTRACT

Improved assemblies, systems, and methods provide an implantable pulse generator for prosthetic or therapeutic stimulation of muscles, nerves, or central nervous system tissue, or any combination. The implantable pulse generator is sized and configured to be implanted subcutaneous a tissue region. The implantable pulse generator includes an electrically conductive case of a laser welded titanium material. Control circuitry is located within the case, the control circuitry including a rechargeable power source, a receive coil for receiving an RF magnetic field to recharge the power source, and a microcontroller for control of the implantable pulse generator. Improved assemblies, systems, and methods also provide a stimulation system for prosthetic or therapeutic stimulation of muscles, nerves, or central nervous system tissue, or any combination. The stimulation system provides at least one electrically conductive surface, a lead connected to the electrically conductive surface, and an implantable pulse generator electrically connected to the lead.

22 Claims, 10 Drawing Sheets

U.S. PATENT DOCUMENTS

| | | | |
|---|---|---|---|
| 5,722,999 | A | 3/1998 | Snell |
| 6,061,596 | A | 5/2000 | Richmond et al. |
| 6,091,995 | A | 7/2000 | Ingle et al. |
| 6,169,925 | B1 | 1/2001 | Villaseca et al. |
| 6,181,965 | B1 | 1/2001 | Loeb et al. |
| 6,185,452 | B1 | 2/2001 | Schulman et al. |
| 6,208,894 | B1 | 3/2001 | Schulman et al. |
| 6,216,038 | B1 | 4/2001 | Hartlaub et al. |
| 6,240,316 | B1 | 5/2001 | Richmond et al. |
| 6,308,101 | B1 | 10/2001 | Faltys et al. |
| 6,345,202 | B2 | 2/2002 | Richmond et al. |
| 6,360,750 | B1 | 3/2002 | Gerber et al. |
| 6,381,496 | B1 | 4/2002 | Meadows et al. |
| 6,450,172 | B1 | 9/2002 | Hartlaub et al. |
| 6,505,074 | B2 | 1/2003 | Boveja et al. |
| 6,516,227 | B1 | 2/2003 | Meadows et al. |
| 6,535,766 | B1 | 3/2003 | Thompson et al. |
| 6,553,263 | B1 * | 4/2003 | Meadows et al. ............. 607/61 |
| 6,622,048 | B1 * | 9/2003 | Mann et al. .................. 607/46 |
| 6,650,943 | B1 | 11/2003 | Whitehurst et al. |
| 6,652,449 | B1 | 11/2003 | Gross et al. |
| 6,735,474 | B1 | 5/2004 | Loeb et al. |
| 6,735,475 | B1 | 5/2004 | Whitehurst et al. |
| 6,862,480 | B2 | 3/2005 | Cohen et al. |
| 6,868,288 | B2 | 3/2005 | Thompson |
| 6,920,359 | B2 | 7/2005 | Meadows et al. |
| 6,937,894 | B1 | 8/2005 | Isaac et al. |
| 6,941,171 | B2 | 9/2005 | Mann et al. |
| 6,999,819 | B2 | 2/2006 | Swoyer et al. |
| 2003/0018365 | A1 | 1/2003 | Loeb |
| 2004/0088024 | A1 | 5/2004 | Firlik et al. |
| 2005/0055063 | A1 | 3/2005 | Loeb et al. |
| 2005/0143787 | A1 | 6/2005 | Boveja et al. |
| 2005/0149146 | A1 | 7/2005 | Boveja et al. |
| 2006/0025829 | A1 | 2/2006 | Armstrong et al. |
| 2006/0122660 | A1 * | 6/2006 | Boveja et al. ................ 607/40 |

OTHER PUBLICATIONS

2005 Biocontrol Medical article: "Lower Urinary Tract," Israel Nissenkorn and Peter R. De Jong, pp. 1253-1258.

Mar. 2002 Physician's Manual; Cyberonics Model 201 NeuroCybernetic Prosthesis (NCP) Programming Wand, pp. 1-18.

Aug. 2002 Physician's Manual; Cyberonics Models 100 and 101 NeuroCybernetic Prosthesis System, NCP Pulse Generator, pp. 1-92.

2005 Advanced Neuromodulation Systems, Inc.; ANS Medical—Determining chronic pain causes and treatments; website: http://www.ans-medical.com/medicalprofessional/physician/rechargeableipgsystems.cfm.

2004 Advanced Bionics Corpporation Summary of Safety and Effectiveness, pp. 1-18.

2004 Advanced Bionics Corporation Physician Implant Manual.

2005 Cyberonics VNS Therapy website: http://www.vnstherapy.com/Epilepsy/hcp/forsurgeons/implantedcomponents.aspx.

2004 Advanced Bionics Corporation Patient System Handbook.

Oct. 2001 Advanced Neuromodulation Systems, Inc. ANS Genesis Neurostimulation System Programmer User's Guide.

Nov. 21, 2001 Advanced Neuromodulation Systems, Inc. (ANS) Summary of Safety and Effectiveness Data, pp. 1-17.

* cited by examiner

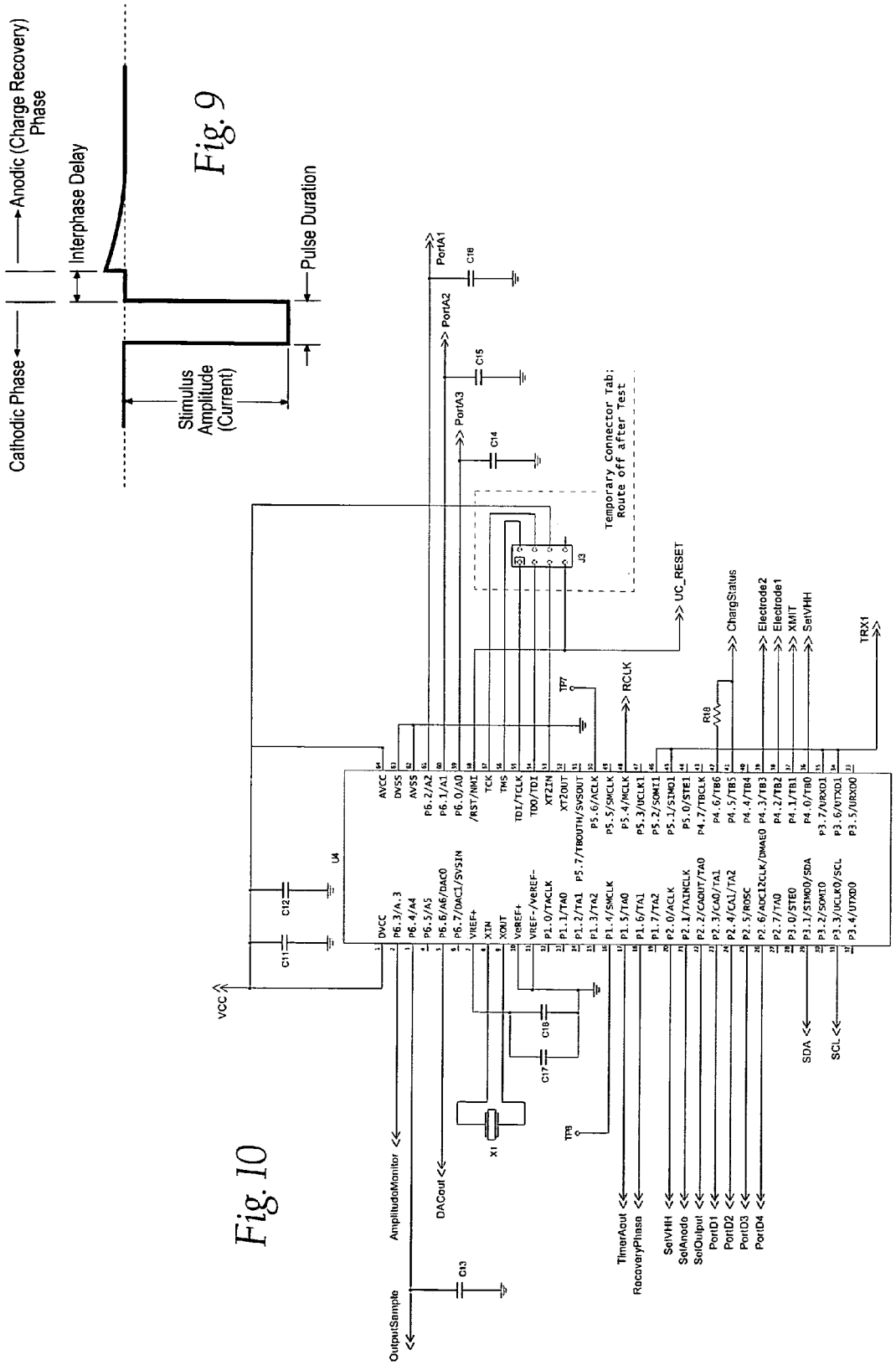

though these small implantable stimulation devices have a reduced physical size, their application to a wide range of neuromuscular stimulation application is limited. Their micro size extremely limits their ability to maintain adequate stimulation strength for an extended period without the need for frequent recharging of their internal power supply (battery). Additionally, their very small size limits the tissue volumes through which stimulus currents can flow at a charge density adequate to elicit neural excitation. This, in turn, limits or excludes many applications.

IMPLANTABLE PULSE GENERATOR FOR PROVIDING FUNCTIONAL AND/OR THERAPEUTIC STIMULATION OF MUSCLES AND/OR NERVES AND/OR CENTRAL NERVOUS SYSTEM TISSUE

RELATED APPLICATION

This application claims the benefit of U.S. Provisional Patent Application Ser. No. 60/578,742, filed Jun. 10, 2004, and entitled "Systems and Methods for Bilateral Stimulation of Left and Right Branches of the Dorsal Genital Nerves to Treat Dysfunctions, Such as Urinary Incontinence" and U.S. Provisional Patent Application Ser. No. 60/599,193, filed Aug. 5, 2004, and entitled "Implantable Pulse Generator for Providing Functional and/or Therapeutic Stimulation of Muscles and/or Nerves" and U.S. Provisional Patent Application Ser. No. 60/680,598, filed May 13, 2005, and entitled "Implantable Pulse Generator for Providing Functional and/or Therapeutic Stimulation of Muscles and/or Nerves and/or Central Nervous System Tissue," which are incorporated herein by reference.

FIELD OF INVENTION

This invention relates to systems and methods for providing stimulation of central nervous system tissue, muscles, or nerves, or combinations thereof.

BACKGROUND OF THE INVENTION

Neuromuscular stimulation (the electrical excitation of nerves and/or muscle to directly elicit the contraction of muscles) and neuromodulation stimulation (the electrical excitation of nerves, often afferent nerves, to indirectly affect the stability or performance of a physiological system) and brain stimulation (the stimulation of cerebral or other central nervous system tissue) can provide functional and/or therapeutic outcomes. While existing systems and methods can provide remarkable benefits to individuals requiring neuromuscular or neuromodulation stimulation, many limitations and issues still remain. For example, existing systems often can perform only a single, dedicated stimulation function.

A variety of products and treatment methods are available for neuromuscular stimulation and neuromodulation stimulation. As an example, neuromodulation stimulation has been used for the treatment of urinary incontinence. Urinary incontinence is a lower pelvic region disorder and can be described as a failure to hold urine in the bladder under normal conditions of pressure and filling. The most common forms of the disorder can arise from either a failure of muscles around the bladder neck and urethra to maintain closure of the urinary outlet (stress incontinence) or from abnormally heightened commands from the spinal cord to the bladder that produce unanticipated bladder contractions (urge incontinence).

There exists both external and implantable devices for the purpose of neuromodulation stimulation for the treatment of urinary urge incontinence. The operation of these devices typically includes the use of an electrode placed either on the external surface of the skin, a vaginal or anal electrode, or a surgically implanted electrode. Although these modalities have shown the ability to provide a neuromodulation stimulation with positive effects, they have received limited acceptance by patients because of their limitations of portability, limitations of treatment regimes, and limitations of ease of use and user control.

Implantable devices have provided an improvement in the portability of neuromodulation stimulation devices, but there remains the need for continued improvement. Implantable stimulators described in the art have additional limitations in that they are challenging to surgically implant because they are relatively large; they require direct skin contact for programming and for turning on and off. In addition, current implantable stimulators are expensive, owing in part to their limited scope of usage.

These implantable devices are also limited in their ability to provide sufficient power which limits their use in a wide range of neuromuscular stimulation, and limits their acceptance by patients because of a frequent need to recharge a power supply and to surgically replace the device when batteries fail.

More recently, small, implantable microstimulators have been introduced that can be injected into soft tissues through a cannula or needle. Although these small implantable stimulation devices have a reduced physical size, their application to a wide range of neuromuscular stimulation application is limited. Their micro size extremely limits their ability to maintain adequate stimulation strength for an extended period without the need for frequent recharging of their internal power supply (battery). Additionally, their very small size limits the tissue volumes through which stimulus currents can flow at a charge density adequate to elicit neural excitation. This, in turn, limits or excludes many applications.

It is time that systems and methods for providing neuromuscular stimulation address not only specific prosthetic or therapeutic objections, but also address the quality of life of the individual requiring neuromuscular and neuromodulation stimulation.

SUMMARY OF THE INVENTION

The invention provides improved assemblies, systems, and methods for providing prosthetic or therapeutic stimulation of central nervous system tissue, muscles, or nerves, or muscles and nerves.

One aspect of the invention provides a stimulation assembly sized and configured to provide prosthetic or therapeutic stimulation of central nervous system tissue, muscles, or nerves, or muscles and nerves. The stimulation assembly includes an implantable pulse generator (IPG) attached to at least one lead and one electrode. The implantable pulse generator is implanted subcutaneously in tissue, preferably in a subcutaneous pocket located remote from the electrode. The electrode is implanted in electrical conductive contact (i.e., the electrode proximity to the excitable tissue allows current flow from the electrode to excite the tissue/nerve) with at least one functional grouping of neural tissue, muscle, or at least one nerve, or at least one muscle and nerve. The lead is tunneled subcutaneously in order to electrically connect the implantable pulse generator to the electrode.

Another aspect of the invention provides improved assemblies, systems, and methods for providing a universal device which can be used for many specific clinical indications requiring the application of pulse trains to muscle and/or nervous tissue for therapeutic (treatment) or functional restoration purposes. Most of the components of the implantable pulse generator are desirably sized and configured so that they can accommodate several different indications, with no or only minor change or modification. Technical features of the implantable pulse generator device include a secondary power source and/or primary power source for improved service life, wireless telemetry for programming and interrogation, a single or limited number of stimulus output stage(s) for pulse generation that are directed to one or more output channels, a lead connection header to provide reliable and easy connection and replacement of the lead/electrode, a programmable microcontroller for timing and control of the implantable pulse generator device functions, and power management circuitry for efficient recharging of the secondary power source and the distribution of appropriate voltages and currents to other circuitry, all of which are incorporated within a small composite case for improved quality of life and ease of implantation.

In one embodiment, the implantable pulse generator comprises an electrically conductive case, and includes a header that carries a plug-in receptacle(s) for attachment of a lead(s) and an antenna for transmission and reception of wireless telemetry signals. Within the case is located a circuit that generates electrical stimulation waveforms, a rechargeable battery, including recharging circuitry, a wireless telemetry circuit, and a programmable microcontroller which carries embedded code.

In one embodiment, an implantable pulse generator includes improved power management circuitry and operating modes for extended service life. The power management circuitry is generally responsible for recovery of power from an RF magnetic field applied externally over the implantable pulse generator, for charging and monitoring the rechargeable battery, and for the distribution of appropriate voltages and currents to other circuitry in the implantable pulse generator. The power management circuitry (through the use of logic and algorithms implemented by the microcontroller) communicates with an implantable pulse generator charger outside the body through the wireless telemetry communications link. The efficient recharging of the secondary power source (rechargeable battery) is accomplished by adjusting the strength of the RF magnetic field generated by the externally mounted implantable pulse generator charger in response to the magnitude of the voltage recovered by the implantable pulse generator and the power demands of the implantable pulse generator's battery. The power management may include operating modes configured to operate the implantable pulse generator at its most efficient power consumption throughout the storage and operation of the implantable pulse generator. These modes selectively disable or shut down circuit functions that are not needed. The modes may include, but are not limited to IPG Active and Charging, IPG Active, and IPG Dormant.

In one embodiment, an implantable pulse generator incorporates wireless telemetry. Wireless telemetry allows the implantable pulse generator to wirelessly interact with a clinician programmer, a clinician programmer derivative, a patient controller, and an implantable pulse generator charger, for example. The wireless telemetry allows a clinician to transmit stimulus parameters, regimes, and other setting to the implantable pulse generator before or after it has been implanted. The wireless telemetry also allows the clinician to retrieve information stored in the implantable pulse generator about the patient's usage of the implantable pulse generator and information about any modifications to the settings of the implantable pulse generator made by the patient. The wireless telemetry also allows the patient controller operated by the user to control the implantable pulse generator, both stimulus parameters and settings in the context of a therapeutic application, or the real-time stimulus commands in the case of a neural prosthetic application. In addition, the wireless telemetry allows the implantable pulse generator to communicate with the recharger (implantable pulse generator charger) during a battery recharge in order to adjust the recharging parameters if necessary, which provides for an efficient and effective recharge. In addition, the wireless telemetry allows the operating program of the implantable pulse generator, i.e., the embedded executable code which incorporates the algorithms and logic for the operation of the implantable pulse generator, to be installed or revised after the implantable pulse generator has been assembled, tested, sterilized, and perhaps implanted. This feature could be used to provide flexibility to the manufacturer in the factory and perhaps to a representative of the manufacturer in the clinical setting.

In one embodiment, an implantable pulse generator provides a clinician programmer incorporating technology based on industry-standard hand-held computing platforms. The clinician programmer allows the clinician or physician to set parameters in the implantable pulse generator (IPG) relating to the treatment of the approved indication. The clinician programmer uses the wireless telemetry feature of the implantable pulse generator to bi-directionally communicate to the implantable pulse generator. In addition, additional features are contemplated based on the ability of the clinician programmer to interact with industry standard software and networks to provide a level of care that improves the quality of life of the patient and would otherwise be unavailable. Such features, using subsets of the clinician programmer software, might include the ability of the clinician or physician to remotely monitor and adjust parameters using the Internet or other known or future developed networking schemes. A clinician programmer derivative (or perhaps a feature included in the implantable pulse generator charger) would connect to the patient's computer in their home through an industry standard network such as the Universal Serial Bus (USB), where in turn an applet downloaded from the clinician's server would contain the necessary code to establish a reliable transport level connection between the implantable pulse generator and the clinician's client software, using the clinician programmer derivative as a bridge. Such a connection may also be established through separately installed software. The clinician or physician could then view relevant diagnostic information, such as the health of the unit or its current efficacy, and then direct the patient to take the appropriate action. Such a feature would save the clinician, the patient and the health care system substantial time and money by reducing the number of office visits during the life of the implant.

Other features of the clinician programmer, based on an industry standard platform, might include the ability to connect to the clinician's computer system in his or her office. Such features may take advantage of the Conduit connection employed by Palm OS® based devices. Such a connection then would transfer relevant patient data to the host computer or server for electronic processing and archiving. With a feature as described here, the clinician programmer then becomes an integral link in an electronic chain that provides better patient service by reducing the amount of paperwork that the physician's office needs to process on each office visit. It also improves the reliability of the service since it reduces the chance of mis-entered or mis-placed information, such as the record of the parameter setting adjusted during the visit.

Other features and advantages of the inventions are set forth in the following specification and attached drawings.

BRIEF DESCRIPTION OF THE DRAWINGS

FIG. 9 is a graphical view of a desirable biphasic stimulus pulse output of the implantable pulse generator for use with the system shown in FIG. 1.

FIG. 10 is a circuit diagram showing a possible circuit for the microcontroller used with the implantable pulse generator shown in FIGS. 2A and 2B.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with providing stimulation of central nervous system tissue, muscles, or nerves, or muscles and nerves for prosthetic or therapeutic purposes. That is because the features and advantages that arise due to the invention are well suited to this purpose. Still, it should be appreciated that the various aspects of the invention can be applied to achieve other objectives as well.

I. Stimulation Assembly

A. System Overview

Figure 1:
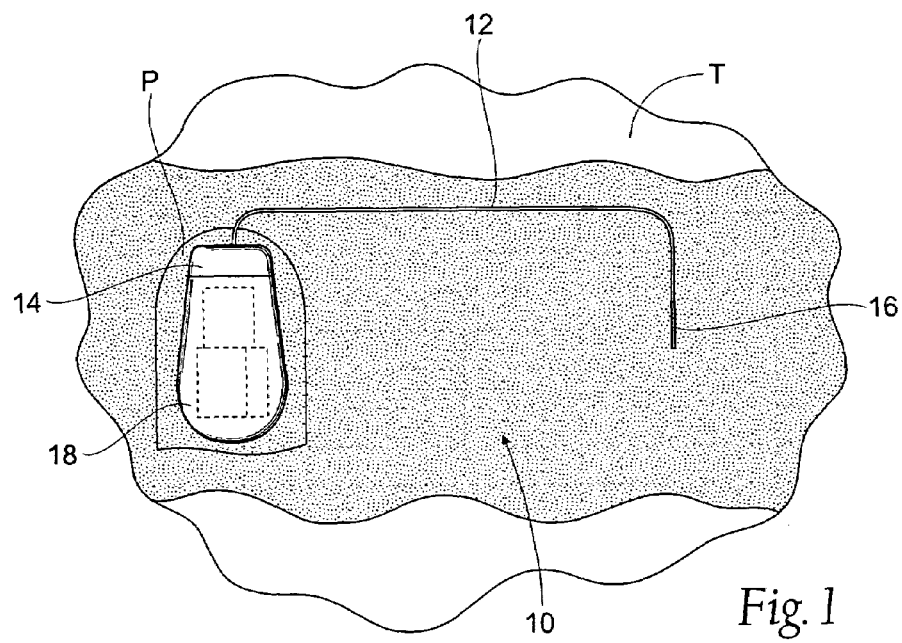
FIG. 1 is a view of a stimulation assembly that provides electrical stimulation to central nervous system tissue, muscles and/or nerves inside the body using a general purpose implantable pulse generator.

FIG. 1 shows an assembly 10 for stimulating a central nervous system tissue, nerve, or a muscle, or a nerve and a muscle for therapeutic (treatment) or functional restoration purposes. The assembly includes an implantable lead 12 coupled to an implantable pulse generator or IPG 18. The lead 12 and the implantable pulse generator 18 are shown implanted within a tissue region T of a human or animal body.

The distal end of the lead 12 includes at least one electrically conductive surface, which will in shorthand be called an electrode 16. The electrode 16 is implanted in electrical conductive contact with at least one functional grouping of neural tissue, muscle, or at least one nerve, or at least one muscle and nerve. The implantable pulse generator 18 includes a connection header 14 that desirably carries a plug-in receptacle for the lead 12. In this way, the lead 12 electrically connects the electrode 16 to the implantable pulse generator 18.

The implantable pulse generator 18 is sized and configured to be implanted subcutaneously in tissue, desirably in a subcutaneous pocket P, which can be remote from the electrode 16, as FIG. 1 shows. Desirably, the implantable pulse generator 18 is sized and configured to be implanted using a minimally invasive surgical procedure.

The surgical procedure may be completed in a number of steps. For example, once a local anesthesia is established, the electrode 16 is positioned at the target site. Next, a subcutaneous pocket P is made and sized to accept the implantable pulse generator 18. The pocket P is formed remote from the electrode 16. Having developed the subcutaneous pocket P for the implantable pulse generator 18, a subcutaneous tunnel is formed for connecting the lead 12 and electrode 16 to the implantable pulse generator 18. The lead 12 is routed through the subcutaneous tunnel to the pocket site P where the implantable pulse generator 18 is to be implanted. The lead 12 is then coupled to the implantable pulse generator 18, and both the lead 12 and implantable pulse generator 18 are placed into the subcutaneous pocket, which is sutured closed.

Figure 2A:
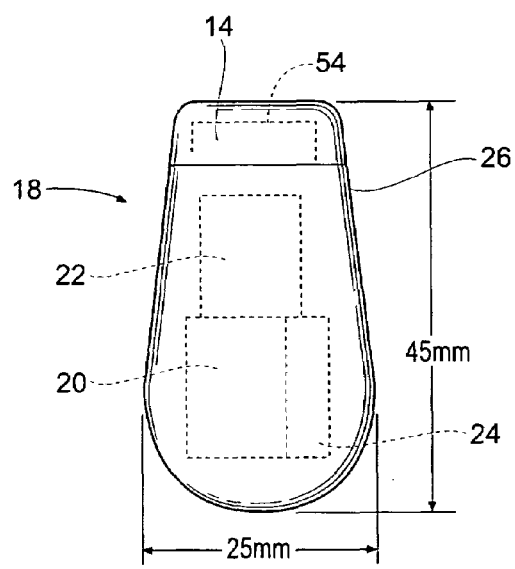
FIG. 2A is a front view of the general purpose implantable pulse generator shown in FIG. 1.
Figure 2B:
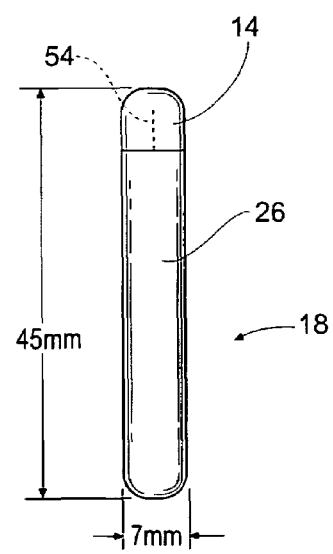
FIG. 2B is a side view of the general purpose implantable pulse generator shown in FIG. 2A.

As FIGS. 2A and 2B shows, the implantable pulse generator 18 includes a circuit 20 that generates electrical stimulation waveforms. An on-board, rechargeable battery 22 desirably provides the power. The implantable pulse generator 18 also desirably includes an on-board, programmable microcontroller 24, which carries embedded code. The code expresses pre-programmed rules or algorithms under which the desired electrical stimulation waveforms are generated by the circuit 20. The implantable pulse generator 18 desirably includes an electrically conductive case 26, which can also serve as the return electrode for the stimulus current introduced by the lead/electrode when operated in a monopolar configuration.

According to its programmed rules, when switched on, the implantable pulse generator 18 generates prescribed stimulation waveforms through the lead 12 and to the electrode 16. These stimulation waveforms stimulate the central nervous system tissue, muscle, nerve, or both nerve and muscle tissue that lay in electrical conductive contact (i.e., within close proximity to the electrode surface where the current densities are high) with the electrode 16, in a manner that achieves the desired therapeutic (treatment) or functional restoration result. As previously discussed, urinary incontinence is just one example of a functional restoration result. Additional examples of desirable therapeutic (treatment) or functional restoration indications will be described in greater detail in section II.

The assembly 10 may also include additional operative components, such as but not limited to, a clinician programmer, a clinician programmer derivative, a patient controller, and an implantable pulse generator charger, each of which will be discussed later.

B. The Implantable Pulse Generator

Desirably, the size and configuration of the implantable pulse generator 18 makes possible its use as a general purpose or universal device (i.e., creating a platform technology), which can be used for many specific clinical indications requiring the application of pulse trains to central nervous system tissue, muscle and/or nervous tissue for therapeutic (treatment) or functional restoration purposes. Most of the components of the implantable pulse generator 18 are desirably sized and configured so that they can accommodate several different indications, without major change or modification. Examples of components that desirably remain unchanged for different indications include the case 26, the battery 22, the power management circuitry 40 for recharging the battery 22, the microcontroller 24, much of the software (firmware) of the embedded code, and the stimulus power supply. Thus, a new indication may require only changes to the programming of the microcontroller 24. Most desirably, the particular code is remotely embedded in the microcontroller 24 after final assembly, packaging, and sterilization of the implantable pulse generator 18.

Certain components of the implantable pulse generator 18 may be expected to change as the indication changes; for example, due to differences in leads and electrodes, the connection header 14 and associated receptacle(s) for the lead may be configured differently for different indications. Other aspects of the circuit 20 may also be modified to accommodate a different indication; for example, the stimulator output stage(s), sensor(s) and/or sensor interface circuitry.

In this way, the implantable pulse generator 18 is well suited for use for diverse indications. The implantable pulse generator 18 thereby accommodates coupling to a lead 12 and an electrode 16 implanted in diverse tissue regions, which are targeted depending upon the therapeutic (treatment) or functional restoration results desired. The implantable pulse generator 18 also accommodates coupling to a lead 12 and an electrode 16 having diverse forms and configurations, again depending upon the therapeutic or functional effects desired. For this reason, the implantable pulse generator can be considered to be general purpose or "universal."

1. Desirable Technical Features

The implantable pulse generator 18 can incorporate various technical features to enhance its universality.

a. Small, Composite Case

According to one desirable technical feature, the implantable pulse generator 18 can be sized small enough to be implanted (or replaced) with only local anesthesia. As FIGS. 2A and 2B show, the functional elements of the implantable pulse generator 18 (e.g., circuit 20, the microcontroller 24, the battery 22, and the connection header 14) are integrated into a small, composite case 26. As FIGS. 2A and 2B show, the case 26 defines a small cross section; e.g., (5 mm to 10 mm thick)×(15 mm to 40 mm wide)×(40 mm to 60 mm long), and an overall weight of approximately 10 to 15 grams. These dimensions make possible implantation of the case 26 with a small incision; i.e., suitable for minimally invasive implantation. Additionally, a larger, but similarly shaped implantable pulse generator might be required for applications with more stimulus channels (thus requiring a larger connection header) and or a larger internal battery.

Figure 3:
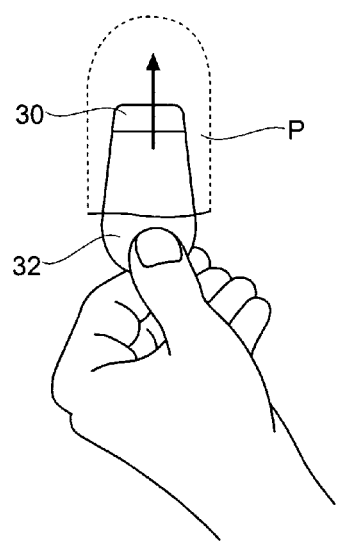
FIG. 3 is a view showing how the geometry of the implantable pulse generator shown in FIGS. 2A and 2B aids in its implantation in a tissue pocket.

The case 26 of the implantable pulse generator 18 is desirably shaped with a smaller end 30 and a larger end 32. As FIG. 3 shows, this geometry allows the smaller end 30 of the case 26 to be placed into the skin pocket P first, with the larger end 32 being pushed in last.

Desirably, the case 26 for the implantable pulse generator 18 comprises a laser welded titanium material. This construction offers high reliability with a low manufacturing cost. The clam shell construction has two stamped or successively drawn titanium case halves that are laser welded around the circuit assembly and battery 22 with feed-thrus. Typically, a molded plastic spacing nest is used to hold the battery 22, the circuit 20, and perhaps a power recovery (receive) coil together and secure them within the titanium case.

The implantable pulse generator 18 shown in FIGS. 2A and 2B includes a clam-shell case 26 having a thickness that is selected to provide adequate mechanical strength while balancing the greater power absorption and shielding effects to the low to medium frequency magnetic field 52 used to transcutaneously recharge the implantable pulse generator Lithium Ion battery 22 with thicker case material (the competing factors are poor transformer action at low frequencies—due to the very low transfer impedances at low frequencies—and the high shielding losses at high frequencies). The selection of the thickness ensures that the titanium case allows adequate power coupling to recharge the secondary power source (described below) of the pulse generator 18 at the target implant depth using a low frequency radio frequency (RF) magnetic field 52 from an implantable pulse generator charger 34 mounted on the skin. Preferably, the implantable pulse generator 18 is implanted at a target implant depth of not less than five millimeters beneath the skin, and not more than fifteen millimeters beneath the skin, although this implant depth may change due to the particular application, or the implant depth may change over time based on physical conditions of the patient, for example.

b. Secondary Power Source

According to one desirable technical feature, the implantable pulse generator 18 desirably possesses an internal battery capacity sufficient to allow operation with recharging not more frequently than once per week for many or most clinical applications. The battery 22 of the implantable pulse generator 18 desirably can be recharged in less than approximately five hours with a recharging mechanism that allows the patient to sleep in bed or carry on most normal daily activities while recharging the battery 22 of the implantable pulse generator 18.

To achieve this feature, the battery 22 of the implantable pulse generator 18 desirably comprises a secondary (rechargeable) power source; most desirably a Lithium Ion battery 22. Given the average quiescent operating current (estimated at 8 µA plus 35 µA for a wireless telemetry receiver pulsing on twice every second) and a seventy percent efficiency of the stimulus power supply, a 1.0 Amp-hr primary cell battery can provide a service life of less than two years, which is too short to be clinically or commercially viable for this indication. Therefore, the implantable pulse generator 18 desirably incorporates a secondary battery 22 (a rechargeable battery), e.g., a Lithium Ion secondary battery that can be recharged transcutaneously. Given representative desirable stimulation parameters (which will be described later), a Lithium Ion secondary battery with a capacity of at least 30 mA-hr will operate for almost three weeks. Lithium Ion implant grade batteries are available from a domestic supplier. A representative battery provides 35 mA-hr in a package configuration that is of appropriate size and shape to fit within the implantable pulse generator 18. The implantable pulse generator 18 could also incorporate a small primary battery to provide current to prevent self-discharge of the secondary battery 22 from dropping its voltage to the point of irreversible damage to the secondary battery.

Figure 4A:
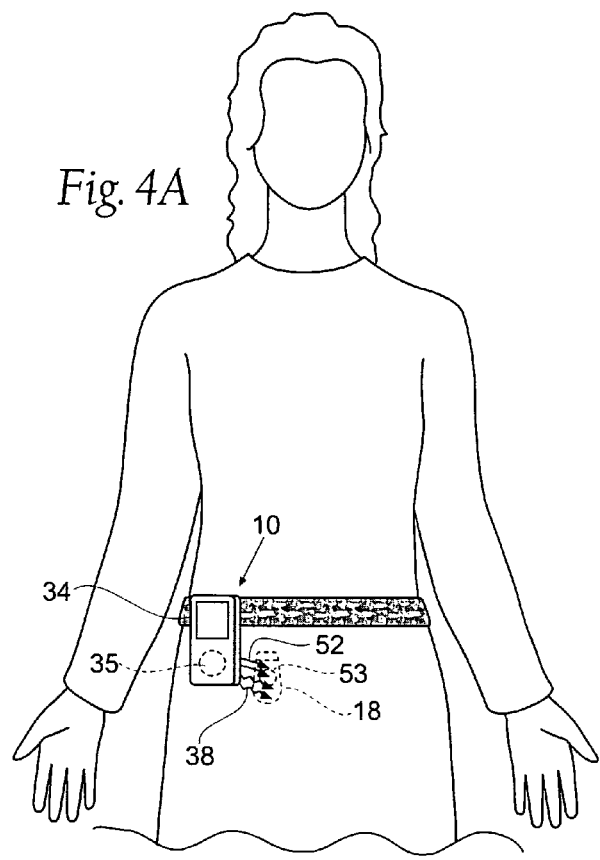
FIG. 4A is a view showing the implantable pulse generator shown in FIGS. 2A and 2B in association with a transcutaneous implantable pulse generator charger (battery recharger) including an integral charging coil which generates the RF magnetic field, and also showing the implantable pulse generator charger using wireless telemetry to communicate with the implantable pulse generator.
Figure 4B:
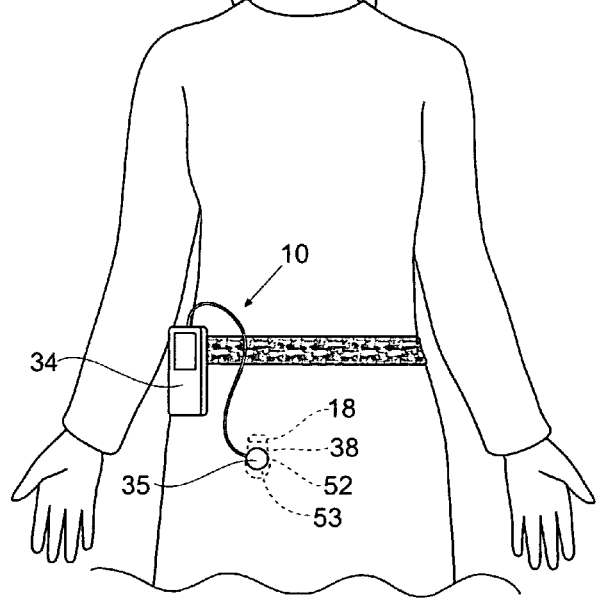
FIG. 4B is an anatomic view showing the transcutaneous implantable pulse generator charger (battery recharger) as shown in FIG. 4A, including a separate, cable coupled charging coil which generates the RF magnetic field, and also showing the implantable pulse generator charger using wireless telemetry to communicate with the implantable pulse generator.

The power for recharging the battery 22 of the implantable pulse generator 18 is provided through the application of a low frequency (e.g., 30 KHz to 300 KHz) RF magnetic field 52 applied by a skin or clothing mounted recharger 34 placed over the implantable pulse generator (see FIGS. 4A and 4B). In one possible application, it is anticipated that the user would wear the recharger 34, including an internal magnetic coupling coil (charging coil) 35, over the implantable pulse generator 18 to recharge the implantable pulse generator 18 (see FIG. 4A). Alternatively, the recharger 34 might use a separate magnetic coupling coil (charging coil) 35 which is placed and/or secured on the skin or clothing over the implantable pulse generator 18 and connected by cable to the recharger 34 (circuitry and battery in a housing) that is worn on a belt or clipped to the clothing (see FIG. 4B).

The charging coil 35 preferably includes a predetermined construction, e.g., desirably 150 to 250 turns, and more desirably 200 turns of six strands of #36 enameled magnetic wire, or the like. Additionally, the charging coil mean diameter is in a range of about 40 millimeters to 60 millimeters, and desirably about 50 millimeters, although the diameter may vary. The thickness of the charging coil 35 as measured perpendicular to the mounting plane is to be significantly less than the diameter, e.g., two to five millimeters, so as to allow the coil to be embedded or laminated in a sheet to facilitate placement on or near the skin. Such a construction will allow for efficient power transfer and will allow the charging coil 35 to maintain a temperature below 41 degrees Celsius.

Figure 4C:
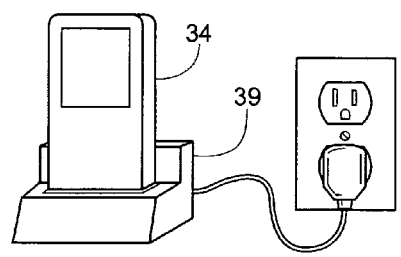
FIG. 4C is a perspective view of the implantable pulse generator charger of the type shown in FIGS. 4A and 4B, with the charger shown docked on a recharge base with the charging base connected to the power mains.

The recharger 34 preferably includes its own internal batteries which may be recharged from the power mains, for example. A charging base 39 may be included to provide for convenient docking and recharging of the system's operative components, including the recharger and the recharger's internal batteries (see FIG. 4C). The implantable pulse generator recharger 34 does not need to be plugged into the power mains while in use to recharge the implantable pulse generator.

Desirably, the implantable pulse generator 18 may be recharged while it is operating and will not increase in temperature by more than two degrees Celsius above the surrounding tissue during the recharging. It is desirable that the recharging of the battery 22 requires not more than six hours, and a recharging would be required between once per month to once per week depending upon the power requirements of the stimulus regime used.

The implantable pulse generator 18 desirably incorporates circuitry and/or programming to assure that the implantable pulse generator 18 will suspend stimulation, and perhaps fall-back to only very low rate telemetry, and eventually suspends all operations when the secondary battery 22 has discharged the majority of it capacity (i.e., only a safety margin charge remains). Once in this dormant mode, the implantable pulse generator can be restored to normal operation only by recharging as shown in FIGS. 4A and 4B.

c. Wireless Telemetry

According to one desirable technical feature, the system or assembly 10 includes an implantable pulse generator 18, which desirably incorporates wireless telemetry (rather that an inductively coupled telemetry) for a variety of functions to be performed within arm's reach of the patient, the functions including receipt of programming and clinical parameters and settings from the clinician programmer 36, communicating usage history to the clinician programmer, providing user control of the implantable pulse generator 18, and for controlling the RF magnetic field 52 generated by the implantable pulse generator charger 34. Each implantable pulse generator may also have a unique signature that limits communication to only the dedicated controllers (e.g., the matched patient controller, implantable pulse generator charger, or a clinician programmer configured for the implantable pulse generator in question).

Figure 6:
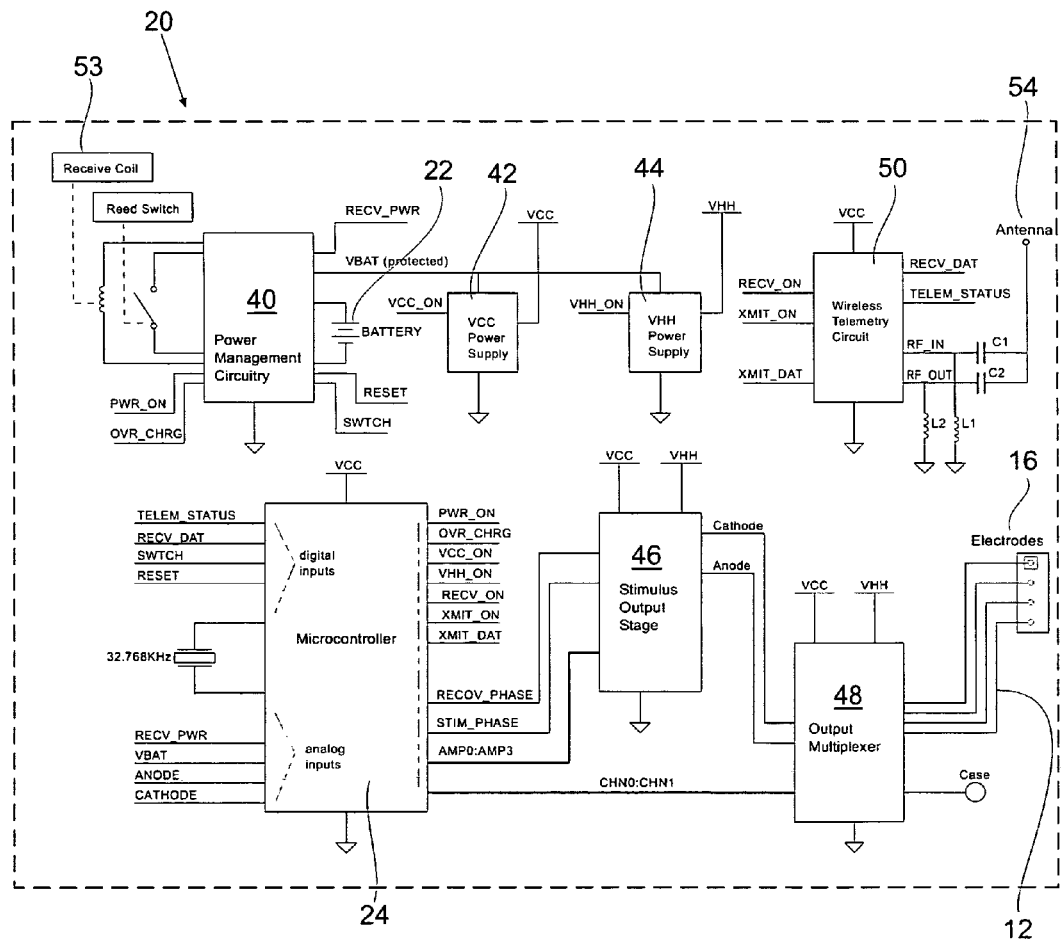
FIG. 6 is a block diagram of a circuit that the implantable pulse generator shown in FIGS. 2A and 2B can incorporate.
Figure 7:
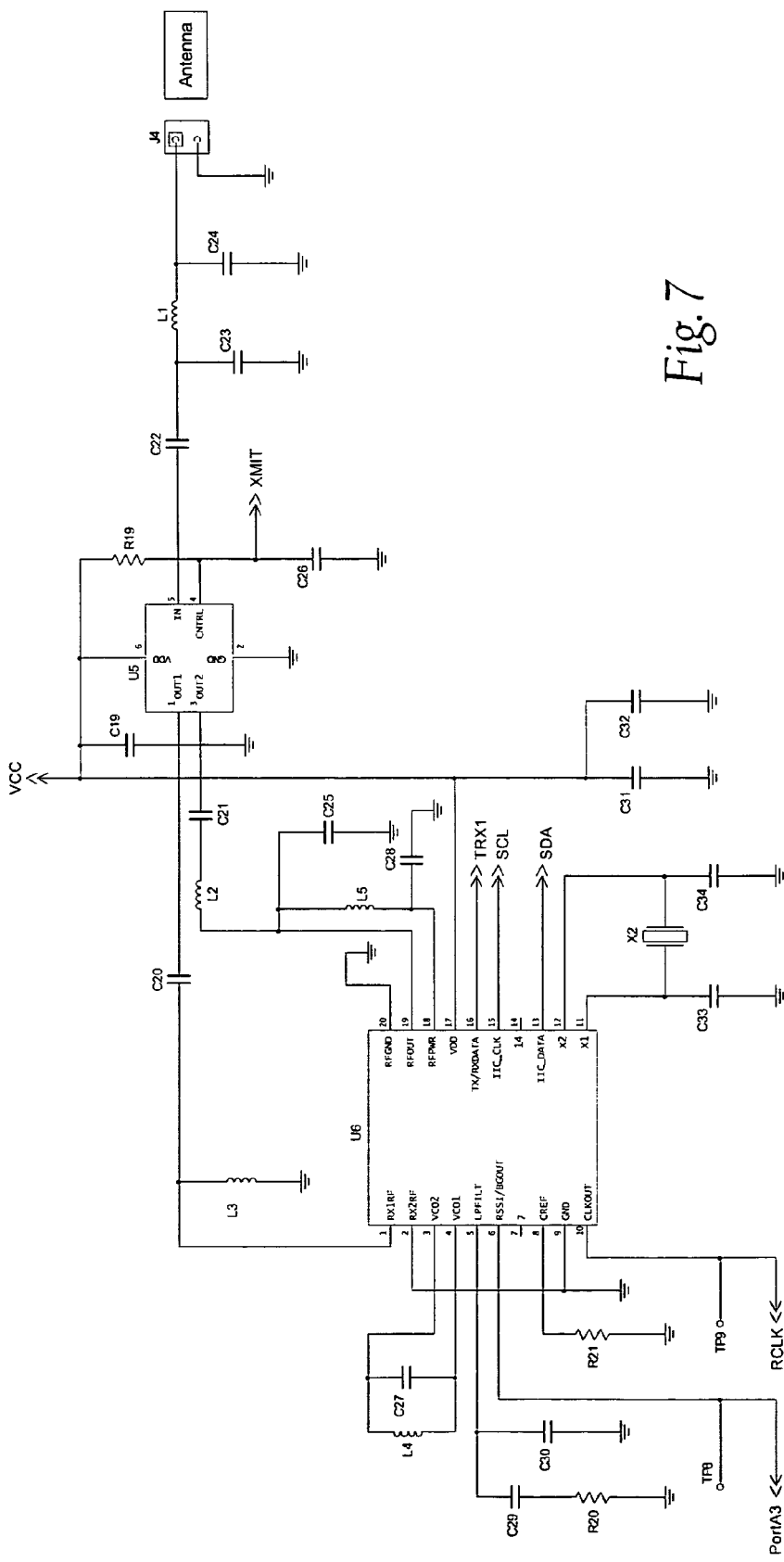
FIG. 7 is a circuit diagram showing a possible circuit for the wireless telemetry feature used with the implantable pulse generator shown in FIGS. 2A and 2B.

The implantable pulse generator 18 desirably incorporates wireless telemetry as an element of the implantable pulse generator circuit 20 shown in FIG. 6. A circuit diagram showing a desired configuration for the wireless telemetry feature is shown in FIG. 7. It is to be appreciated that modifications to this circuit diagram configuration which produce the same or similar functions as described are within the scope of the invention.

Figure 5A:
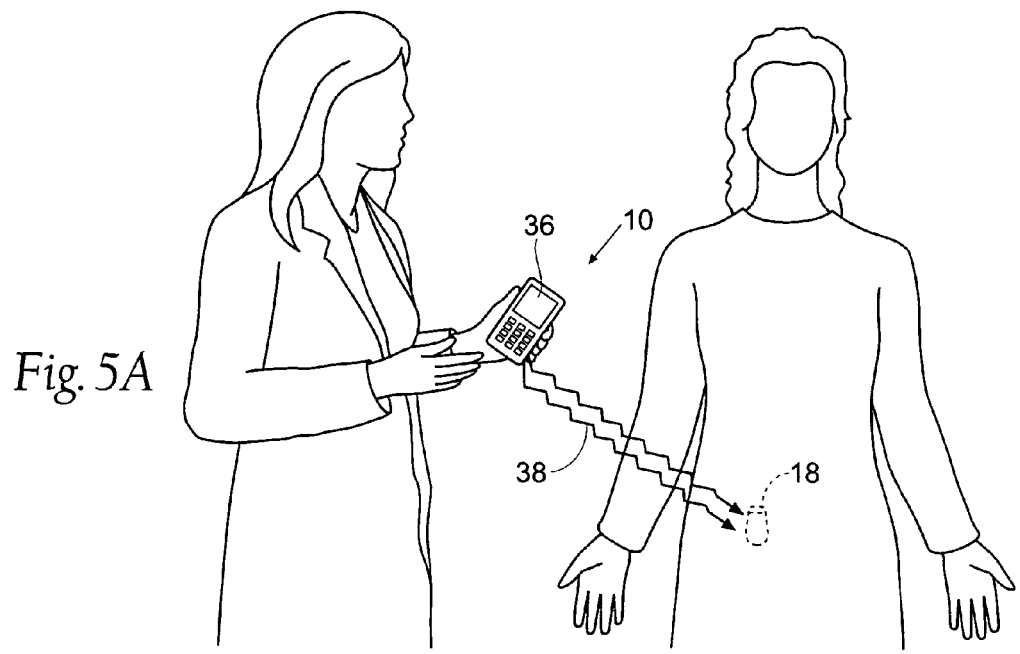
FIG. 5A is an anatomic view showing the implantable pulse generator shown in FIGS. 2A and 2B in association with an external programmer that relies upon wireless telemetry, and showing the programmer's capability of communicating with the implantable pulse generator up to an arm's length away from the implantable pulse generator.

As shown in FIG. 5A, the assembly 10 desirably includes a clinician programmer 36 that, through a wireless telemetry 38, transfers commands, data, and programs into the implantable pulse generator 18 and retrieves data out of the implantable pulse generator 18. In some configurations, the clinician programmer may communicate with more than one implantable pulse generator implanted in the same user.

Figure 5B:
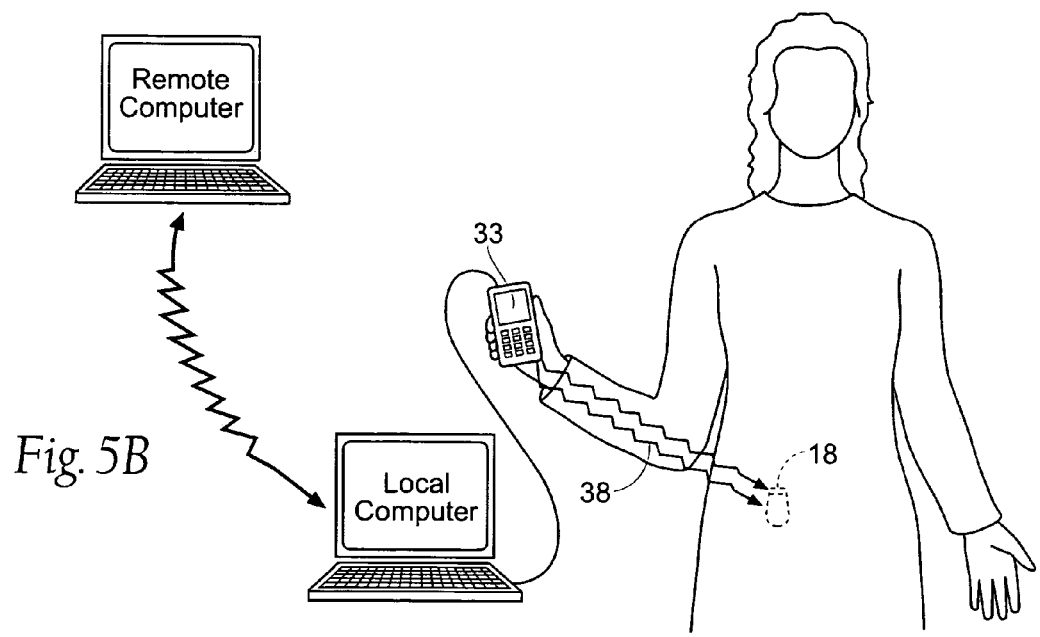
FIG. 5B is a system view of an implantable pulse generator system incorporating a clinician programmer derivative and showing the system's capability of communicating and transferring data over a network, including a remote network.

The clinician programmer 36 may incorporate a custom programmed general purpose digital device, e.g., a custom program, industry standard handheld computing platform or other personal digital assistant (PDA). The clinician programmer 36 can include an on-board microcontroller powered by a rechargeable battery. The rechargeable battery of the clinician programmer 36 may be recharged in the same or similar manner as described and shown for the recharger 34, i.e., docked on a charging base 39 (see FIG. 4C); or the custom electronics of the clinician programmer may receive power from the connected PDA. The microcontroller carries embedded code which may include pre-programmed rules or algorithms that allow a clinician to remotely download program stimulus parameters and stimulus sequences parameters into the implantable pulse generator 18. The microcontroller of the clinician programmer 36 is also desirably able to interrogate the implantable pulse generator and upload usage data from the implantable pulse generator. FIG. 5A shows one possible application where the clinician is using the programmer 36 to interrogate the implantable pulse generator. FIG. 5B shows an alternative application where the clinician programmer, or a clinician programmer derivative 33 intended for remote programming applications and having the same or similar functionality as the clinician programmer, is used to interrogate the implantable pulse generator. As can be seen, the clinician programmer derivative 33 is connected to a local computer, allowing for remote interrogation via a local area network, wide area network, or Internet connection, for example.

Using subsets of the clinician programmer software, features of the clinician programmer 36 or clinician programmer derivative 33 might include the ability of the clinician or physician to remotely monitor and adjust parameters using the Internet or other known or future developed networking schemes. A clinician programmer derivative 33 (or perhaps a feature included in the implantable pulse generator charger) would desirably connect to the patient's computer in their home through an industry standard network such as the Universal Serial Bus (USB), where in turn an applet downloaded from the clinician's server would contain the necessary code to establish a reliable transport level connection between the implantable pulse generator 18 and the clinician's client software, using the clinician programmer derivative 33 as a bridge. Such a connection may also be established through separately installed software. The clinician or physician could then view relevant diagnostic information, such as the health of the unit or its current settings, and then modify the stimulus settings in the implantable pulse generator or direct the patient to take the appropriate action. Such a feature would save the clinician, the patient and the health care system substantial time and money by reducing the number of office visits during the life of the implant.

Other features of the clinician programmer, based on an industry standard platform, might include the ability to connect to the clinician's computer system in his or hers office. Such features may take advantage of the Conduit connection employed by Palm OS based devices. Such a connection then would transfer relevant patient data to the host computer or server for electronic processing and archiving. With a feature as described here, the clinician programmer then becomes an integral link in an electronic chain that provides better patient service by reducing the amount of paperwork that the physician's office needs to process on each office visit. It also improves the reliability of the service since it reduces the chance of mis-entered or mis-placed information, such as the record of the parameter setting adjusted during the visit.

With the use of a patient controller 37 (see FIG. 5C), the wireless link 38 allows a patient to control a limited range of parameters within the implantable pulse generator, such as operation modes/states, increase/decrease or optimize stimulus patterns, or provide open or closed loop feedback from an external sensor or control source. The wireless telemetry 38 also desirably allows the user to interrogate the implantable pulse generator 18 as to the status of its internal battery 22. The full ranges within these parameters may be controlled, adjusted, and limited by a clinician, so the user may not be allowed the full range of possible adjustments.

Figure 5C:
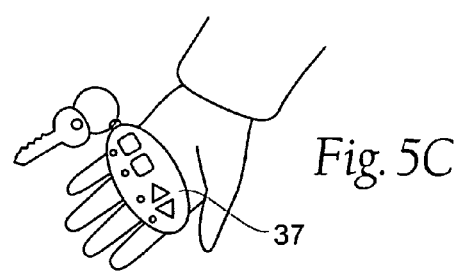
FIG. 5C is a perspective view of one possible type of patient controller that may be used with the implantable pulse generator shown in FIGS. 2A and 2B.

In one embodiment, the patient controller 37 is sized and configured to couple to a key chain, as seen in FIG. 5C. It is to be appreciated that the patient controller 37 may take on any convenient shape, such as a ring on a finger or an attachment to a belt, for example. It may also be desirable to combine both the functions of the implantable pulse generator charger and the patient controller into a single external device.

The recharger 34 shown in FIGS. 4A and 4B may also use wireless telemetry to communicate with the implantable pulse generator 18, so as to adjust the magnitude of the magnetic field 52 to allow optimal recharging of the implantable pulse generator battery 22 while minimizing unnecessary power consumption by the recharger and power dissipation in the implantable pulse generator (through circuit losses and/or through absorption by implantable pulse generator case and construction).

For example, a suitable, low power wireless telemetry transceiver (radio) chip set can operate in the MICS (Medical Implant Communications Service) band (403 MHz to 406 MHz) or other VHF/UHF low power, unlicensed bands. A wireless telemetry link not only makes the task of communicating with the implantable pulse generator 18 easier, but it also makes the link suitable for use in motor control applications where the user issues a command to the implantable pulse generator to produce muscle contractions to achieve a functional goal (e.g., to stimulate ankle flexion to aid in the gait of an individual after a stroke) without requiring a coil or other component taped or placed on the skin over the implanted implantable pulse generator.

Appropriate use of power management techniques is important to the effective use of wireless telemetry. Desirably, the implantable pulse generator is exclusively the communications slave, with all communications initiated by the external controller (the communications master). The receiver chip of the implantable pulse generator is OFF more than 99% of the time and is pulsed on periodically to search for a command from an external controller, including but not limited to the implantable pulse generator charger 34, the clinician programmer 36, and the patient controller 37. Communications protocols include appropriate check and message acknowledgment handshaking to assure the necessary accuracy and completeness of every message. Some operations (such as reprogramming or changing stimulus parameters) require rigorous message accuracy testing and acknowledgement. Other operations, such as a single user command value in a string of many consecutive values, might require less rigorous checking and a more loosely coupled acknowledgement.

The timing with which the implantable pulse generator enables its transceiver to search for RF telemetry from an external controller is precisely controlled (using a time base established by a quartz crystal) at a relatively low rate (e.g., twice per second; i.e., every 500 milliseconds). This allows the external controller to time when the implantable pulse generator responds to a command and then to synchronize its commands with when the implantable pulse generator will be listening for commands. This, in turn, allows commands issued within a short time (seconds to minutes) of the last command to be captured and acted upon without having to 'broadcast' an idle or pause signal for 500 milliseconds before actually issuing the command in order to know that the implantable pulse generator will have enabled its receiver and received the command. Similarly, the communications sequence is configured to have the external controller issue commands in synchronization with when the implantable pulse generator will be listening for a command. Similarly, the command set implemented is selected to minimize the number of messages necessary and the length of each message consistent with the appropriate level of error detection and message integrity monitoring. It is to be appreciated that the monitoring rate may vary faster or slower depending on the application, and may vary over time within a given application.

A suitable radio chip is used for the half duplex wireless communications, e.g., the AMIS-52100 (AMI Semiconductor; Pocatello, Id.). This transceiver chip is designed specifically for the MICS and its European counter-part the ULP-AMI (Ultra Low Power-Active Medical Implant) band. This chip set is optimized by micro-power operation with rapid start-up, and RF 'sniffing' circuitry.

d. Stimulus Output Stage

According to one desirable technical feature, the implantable pulse generator 18 desirably uses a single stimulus output stage (generator) that is directed to one or more output channels (electrode surfaces) by analog switch(es) or analog multiplexer(s). Desirably, the implantable pulse generator 18 will deliver at least two channels of stimulation via a lead/electrode. For applications requiring more stimulus channels, several channels (perhaps up to four) can be generated by a single output stage. In turn, two or more output stages could be used, each with separate multiplexing to multiple channels, to allow an implantable pulse generator with eight or more stimulus channels. The stimulation desirably has a biphasic waveform (net DC current less than 10 µA), amplitude of at least 8 mA, for neuromodulation applications, or 16 mA to 20 mA for muscle stimulation applications, and pulse durations up to 500 microseconds. The stimulus current (amplitude) and pulse duration being programmable on a channel to channel basis and adjustable over time based on a clinically programmed sequence or regime or based on user (patient) commands received via the wireless communications link.

Figure 8:
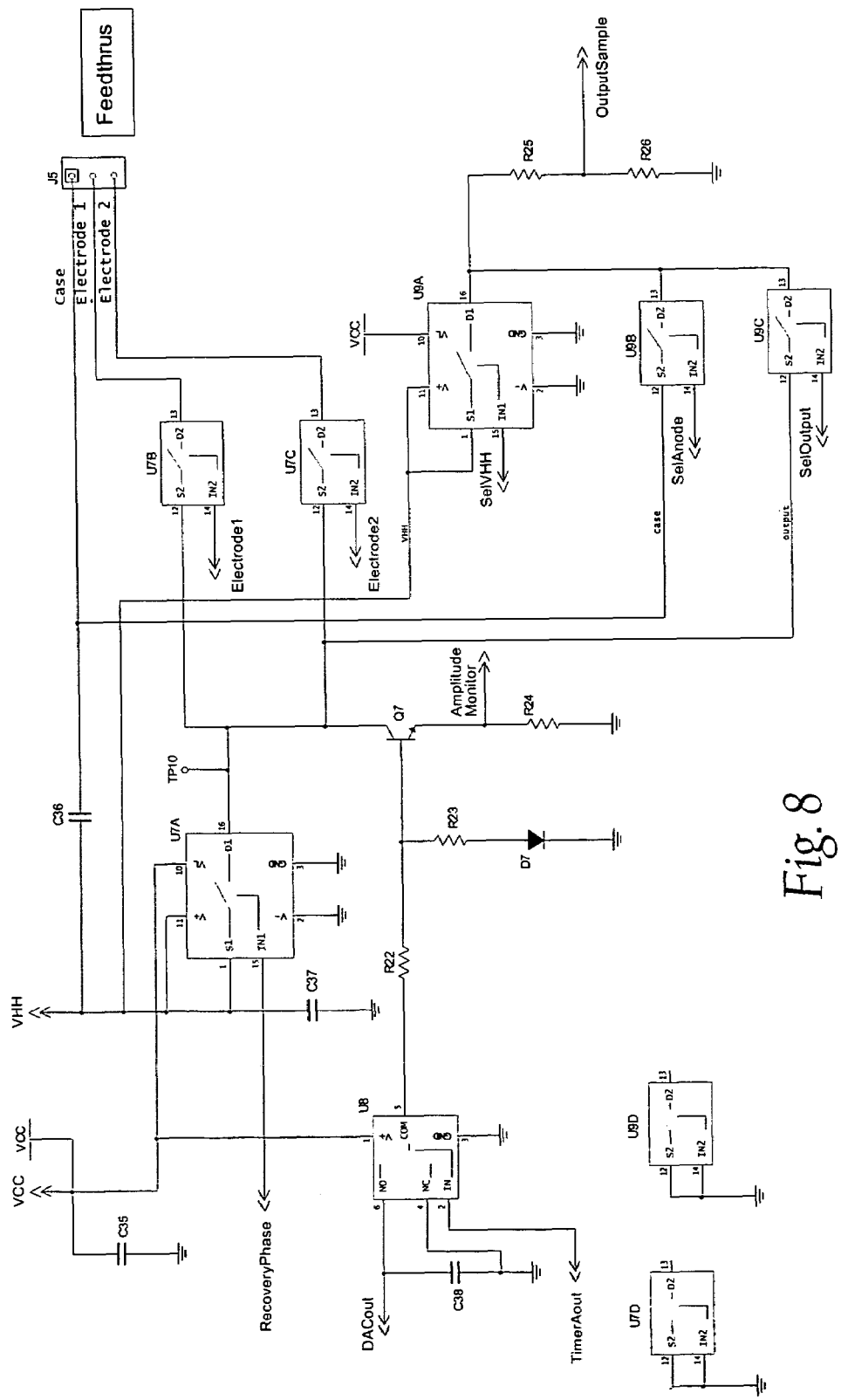
FIG. 8 is a circuit diagram showing a possible circuit for the stimulus output stage and output multiplexing features used with the implantable pulse generator shown in FIGS. 2A and 2B.

A circuit diagram showing a desired configuration for the stimulus output stage feature is shown in FIG. 8. It is to be appreciated that modifications to this circuit diagram configuration which produce the same or similar functions as described are within the scope of the invention.

For neuromodulation/central nervous system applications, the implantable pulse generator 18 desirably has the capability of applying stimulation twenty-four hours per day. A typical stimulus regime for such applications might have a constant stimulus phase, a no stimulus phase, and ramping of stimulus levels between these phases.

Desirably, the implantable pulse generator 18 includes a single stimulus generator (with its associated DC current blocking output capacitor) which is multiplexed to a number of output channels; or a small number of such stimulus generators each being multiplexed to a number of output channels. This circuit architecture allows multiple output channels with very little additional circuitry. A typical, biphasic stimulus pulse is shown in FIG. 6. Note that the stimulus output stage circuitry 46 may incorporate a mechanism to limit the recovery phase current to a small value (perhaps 0.5 mA). Also note that the stimulus generator (and the associated timing of control signals generated by the microcontroller) may provide a delay (typically of the order of 100 microseconds) between the cathodic phase and the recovery phase to limit the recovery phase diminution of the cathodic phase effective at eliciting a neural excitation. The charge recovery phase for any electrode (cathode) must be long enough to assure that all of the charge delivered in the cathodic phase has been returned in the recovery phase, i.e., greater than or equal to five time constants are allowed for the recovery phase. This will allow the stimulus stage to be used for the next electrode while assuring there is no net DC current transfer to any electrode. Thus, the single stimulus generator having this characteristic would be limited to four channels (electrodes), each with a maximum frequency of 30 Hz to 50 Hz. This operating frequency exceeds the needs of many indications for which the implantable pulse generator is well suited. For applications requiring more channels (or higher composite operating frequencies, two or more separate output stages might each be multiplexed to multiple (e.g., four) electrodes.

e. The Lead Connection Header

According to one desirable technical feature, the implantable pulse generator 18 desirably includes a lead connection header 14 for connecting the lead(s) 12 that will enable reliable and easy replacement of the lead/electrode (see FIGS. 2A and 2B), and includes a small antenna 54 for use with the wireless telemetry feature.

The implantable pulse generator desirably incorporates a connection header (top header) 14 that is easy to use, reliable, and robust enough to allow multiple replacements of the implantable pulse generator after many years (e.g., more than ten years) of use. The surgical complexity of replacing an implantable pulse generator is usually low compared to the surgical complexity of correctly placing the implantable lead 12/electrode 16 in proximity to the target nerve/tissue and routing the lead 12 to the implantable pulse generator. Accordingly, the lead 12 and electrode 16 desirably has a service life of at least ten years with a probable service life of fifteen years or more. Based on the clinical application, the implantable pulse generator may not have this long a service life. The implantable pulse generator service life is largely determined by the number of charge-discharge cycles of the Lithium Ion battery 22, and is likely to be three to ten years, based on the usage of the device. Most desirably, the implantable pulse generator 18 has a service life of at least five years.

As described above, the implantable pulse generator preferably will use a laser welded titanium case. As with other active implantable medical devices using this construction, the implantable lead(s) 12 connect to the implantable pulse generator through a molded or cast polymeric connection header 14 (top header). Metal-ceramic or metal-glass feed-thrus maintain the hermetic seal of the titanium capsule while providing electrical contact to the electrical contact(s) of the lead 12/electrode 16.

The standard implantable connectors may be similar in design and construction to the low-profile IS-1 connector system (per ISO 5841-3). The IS-1 connectors have been in use since the late 1980s and have been shown to be reliable and provide easy release and re-connection over several implantable pulse generator replacements during the service life of a single pacing lead. Full compatibility with the IS-1 standard, and mating with pacemaker leads, is not a requirement for the implantable pulse generator.

The implantable pulse generator connection system may include a modification of the IS-1 connector system, which shrinks the axial length dimensions while keeping the format and radial dimensions of the IS-1. For application with more than two electrode conductors, the top header 14 may incorporate one or more connection receptacles each of which accommodate leads with typically four conductors. When two or more leads are accommodated by the header, these lead may exit the connection header in opposite directions (i.e., from opposite sides of the header)

These connectors can be similar to the banded axial connectors used by other multi-polar implantable pulse generators or may follow the guidance of the draft IS-4 implantable connector standard. The design of the implantable pulse generator housing and header 14 preferably includes provisions for adding the additional feed-thrus and larger headers for such indications.

The inclusion of the UHF antenna 54 for the wireless telemetry inside the connection header (top header) 14 is necessary as the shielding offered by the titanium case will severely limit (effectively eliminate) radio wave propagation through the case. The antenna 54 connection will be made through a feed-thru similar to that used for the electrode connections. Alternatively, the wireless telemetry signal may be coupled inside the implantable pulse generator onto a stimulus output channel and coupled to the antenna 54 with passive filtering/coupling elements/methods in the connection header 14.

f. The Microcontroller

According to one desirable technical feature, the implantable pulse generator 18 desirably uses a standard, commercially available micro-power, flash programmable microcontroller 24 or processor core in an application specific integrated circuit (ASIC). This device (or possibly more than one such device for a computationally complex application with sensor input processing) and other large semiconductor components may have custom packaging such as chip-on-board, solder flip chip, or adhesive flip chip to reduce circuit board real estate needs.

Figure 12:
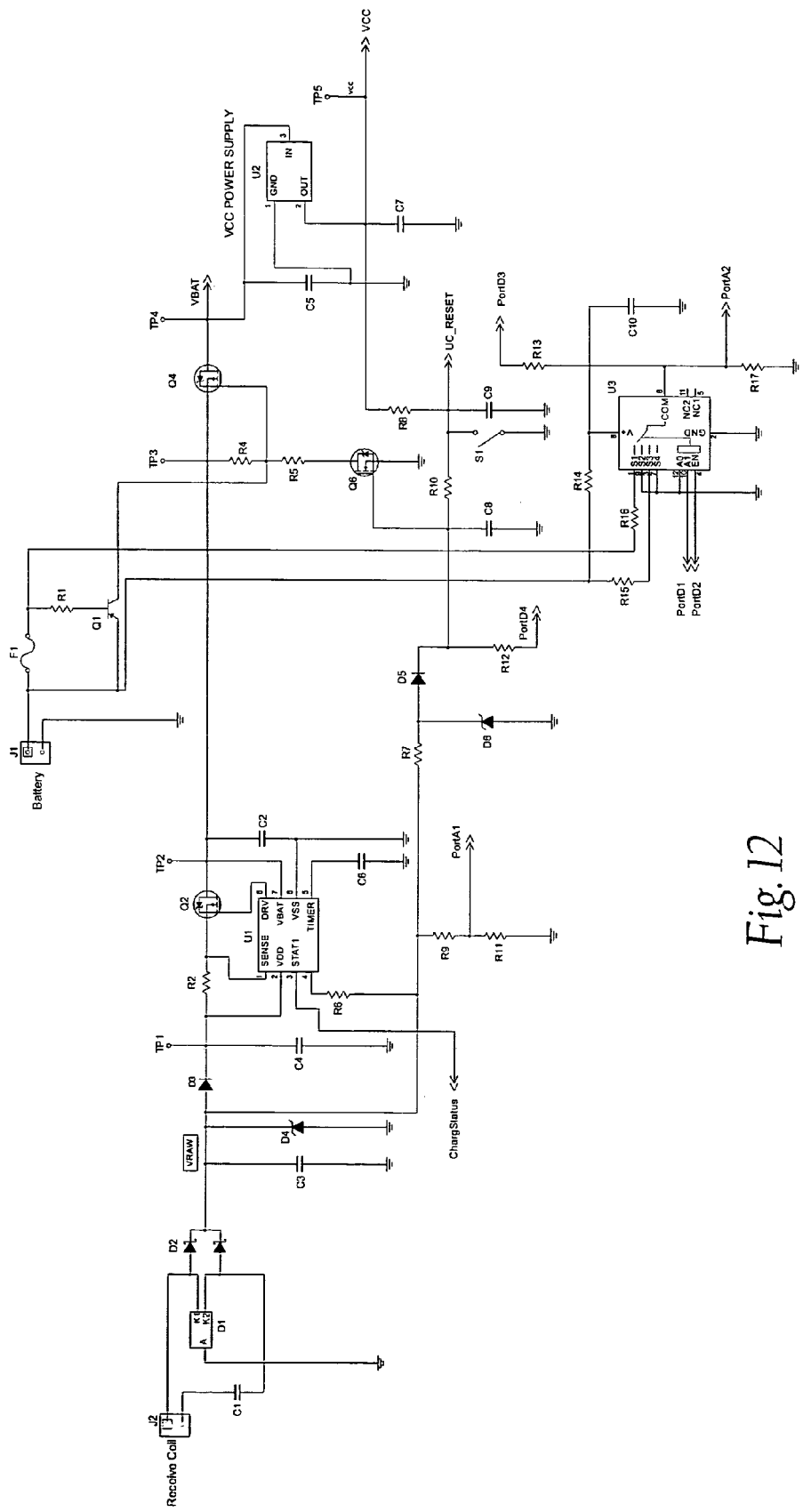
FIG. 12 is a circuit diagram showing a second possible option for a power management sub-circuit where the sub-circuit does not include MOSFET isolation between the battery and charger circuit, the power management sub-circuit being a part of the implantable pulse generator circuit shown in FIG. 6.

A circuit diagram showing a desired configuration for the microcontroller 24 is shown in FIG. 12. It is to be appreciated that modifications to this circuit diagram configuration which produce the same or similar functions as described are within the scope of the invention.

g. Power Management Circuitry

Figure 11:
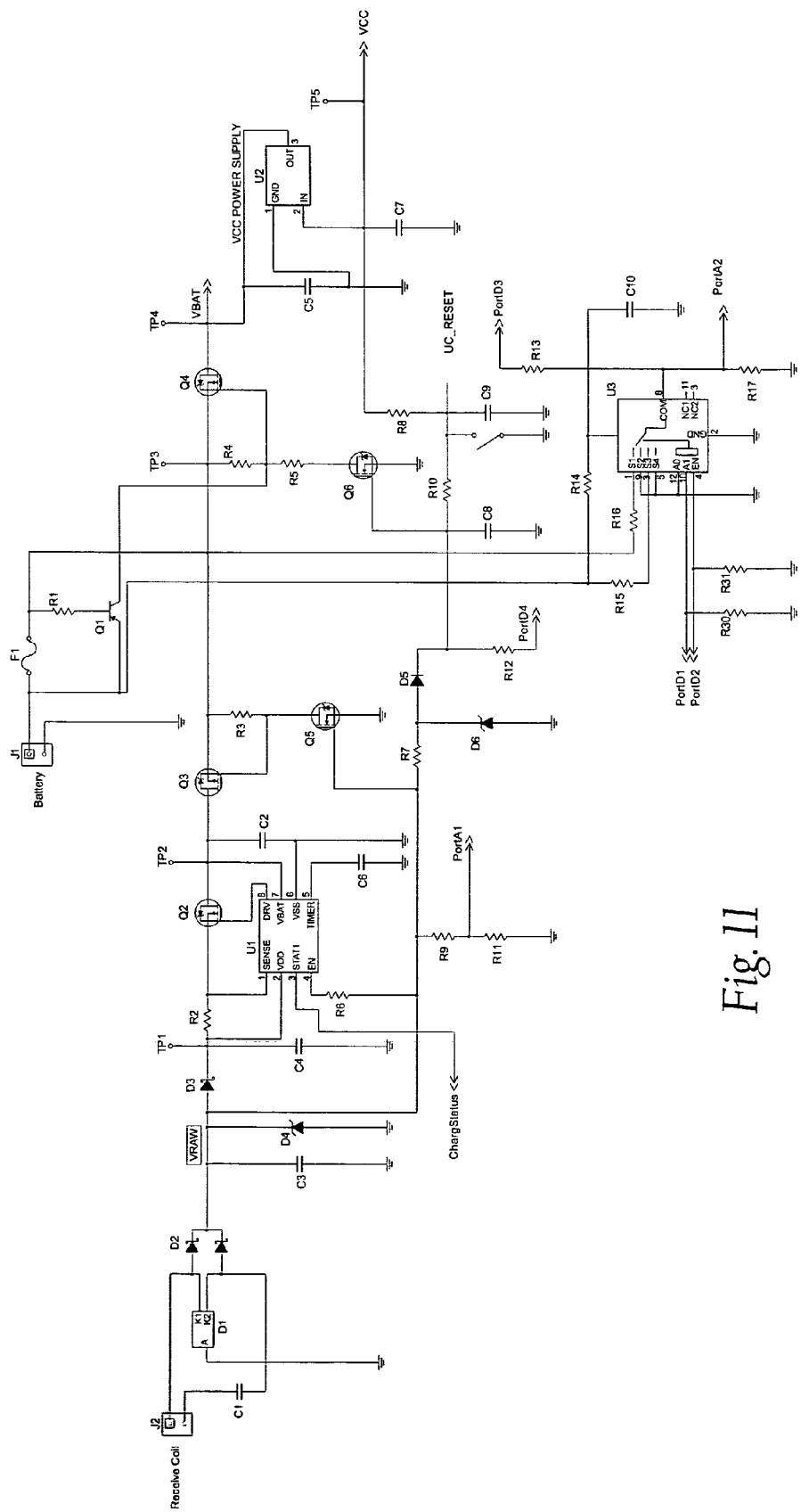
FIG. 11 is a circuit diagram showing one possible option for a power management sub-circuit where the sub-circuit includes MOSFET isolation between the battery and charger circuit, the power management sub-circuit being a part of the implantable pulse generator circuit shown in FIG. 6.

According to one desirable technical feature, the implantable pulse generator 18 desirably includes efficient power management circuitry as an element of the implantable pulse generator circuitry 20 shown in FIG. 6. The power management circuitry is generally responsible for the efficient distribution of power, the recovery of power from the RF magnetic field 52, and for charging and monitoring the Lithium Ion battery 22. In addition, the operation of the implantable pulse generator 18 can be described in terms of having operating modes as relating to the function of the power management circuitry. These modes may include, but are not limited to IPG Active and Charging, IPG Active, and IPG Dormant. These modes will be described below in terms of the principles of operation of the power management circuitry using possible circuit diagrams shown in FIGS. 11 and 12. FIG. 11 shows one possible power management sub-circuit having MOSFET isolation between the battery 22 and the charger circuit. FIG. 12 shows another possible power management sub-circuit diagram without having MOSFET isolation between the battery 22 and the charger circuit. In the circuit without the isolation MOSFET (see FIG. 12), the leakage current of the disabled charge control integrated circuit chip (U1) must be very low to prevent this leakage current from discharging the battery 22 in all modes (including the Dormant Mode). Except as noted, the description of these modes applies to both circuits.

i. IPG Active and Charging Mode

The IPG Active and Charging mode occurs when the implantable pulse generator 18 is being charged. In this mode, the implantable pulse generator is active, i.e., the microcontroller 24 is powered and coordinating wireless communications and may be timing and controlling the generation and delivery of stimulus pulses. The implantable pulse generator 18 may be communicating with the implantable pulse generator charger 34 concerning the magnitude of the battery voltage and the DC voltage recovered from the RF magnetic field 52. The charger 34 uses this data for two purposes: to provide feedback to the user about the proximity of the charging coil 35 to the implanted pulse generator, and to increase or decrease the strength of the RF magnetic field 52. This, in turn, minimizes the power losses and undesirable heating of the implantable pulse generator.

While in the IPG Active and Charging mode, the power management circuitry 40 serves the following primary functions:

(1) provides battery power to the rest of the implantable pulse generator circuitry, (2) recovers power from the RF magnetic field 52 generated by the implantable pulse generator charger 34, (3) provides controlled charging current (from the recovered power) to the battery 22, and (4) communicates with the implantable pulse generator charger 34 via the wireless telemetry link 38 to provide feedback to the user positioning the charging coil 35 over the implantable pulse generator, and to cause the implantable pulse generator charger 34 to increase or decrease the strength of its RF magnetic field 52 for optimal charging of the implantable pulse generator battery 22 (Lithium Ion battery).

i(a) Principles of Operation, IPG Active and Charging Mode i(a)(1) RF voltage is induced in the Receive Coil by the RF magnetic field 52 of the implantable pulse generator charger 34 i(a)(2) Capacitor C1 is in series with the Receive Coil and is selected to introduce a capacitive reactance that compensates (subtracts) the inductive reactance of the Receive Coil i(a)(3) D1-D2 form a full wave rectifier that converts the AC voltage recovered by the Receive Coil into a pulsating DC current flow i(a)(4) This pulsating DC current is smoothed (filtered) by C3 (this filtered DC voltage is labeled VRAW)

i(a)(5) D4 is a zener diode that acts as a voltage limiting device (in normal operation, D4 is not conducting significant current)

i(a)(6) D3 prevents the flow of current from the battery 22 from preventing the correct operation of the Charge Management Circuitry once the voltage recovered from the RF magnetic field is removed. Specifically, current flow from the battery (through Q3 (turned ON), in the case for the circuit of FIG. 11) through the body diode of Q2 would hold ON the charge controller IC (U1). This additional current drain would be present in all modes, including dormant, and would seriously limit battery operating life. Additionally, this battery current pathway would keep Q6 turned ON even if the magnetic reed switch (S1) were closed; thus preventing the isolation of the IPG circuitry from the battery in the dormant mode. In FIG. 11, D3 is desirably a schottky diode because of the lower forward voltage drop; whereas it is desirably a conventional silicone diode in FIG. 12 because of the lower reverse voltage leakage current.

i(a)(7) U1, Q2, R2, C4, C6, and C2 form the battery charger sub-circuit

- U1 is a micropower, Lithium Ion Charge Management Controller chip implementing a constant current phase and constant voltage phase charge regime. This chip desirably incorporates an internal voltage reference of high accuracy (+/−0.5%) to establish the constant voltage charge level. U1 performs the following functions:
- monitors the voltage drop across a series resistor R2 (effectively the current charging the battery 22) to control the current delivered to the battery through the external pass transistor Q2. U1 uses this voltage across R2 to establish the current of the constant current phase (typically the battery capacity divided by five hours), and decreases the current charging the battery as required to limit the battery voltage and effectively transition from constant current phase to constant voltage phase as the battery voltage approaches the terminal voltage, i(a)(8) U1 also includes provisions for timing the duration of the constant current and constant voltage phases and suspends the application of current to the battery 22 if too much time is spent in the phase. These fault timing features of U1 are not used in normal operation.

i(a)(9) In this circuit, the constant voltage phase of the battery charging sequence is timed by the microcontroller 24 and not by U1. The microcontroller monitors the battery voltage and terminates the charging sequence (i.e., tells the implantable pulse generator charger 34 that the implantable pulse generator battery 22 is fully charged) after the battery voltage has been in the constant voltage region for greater than a fixed time period (e.g., 15 to 20 minutes).

i(a) (10) In FIG. 11, Q3 and Q5 are turned ON only when the charging power is present. This effectively isolates the charging circuit from the battery 22 when the externally supplied RF magnetic field 52 is not present and providing power to charge the battery.

i(a)(11) In FIG. 12, U1 is always connected to the battery 22, and the disabled current of this chip is a load on the battery 22 in all modes (including the dormant mode). This, in turn, is a more demanding requirement on the current consumed by U1 while disabled.

i(a) (12) F1 is a fuse that protects against long-duration, high current component failures. In all anticipated transient high current failures, (i.e., soft failures that cause the circuitry to consume high current levels and thus dissipate high power levels; but the failure initiating the high current flow is not permanent and the circuit will resume normal function if the circuit is removed from the power source before damage from overheating occurs), the VBAT circuitry will disconnect the battery 22 from the temporary high load without blowing the fuse. The specific sequence is:

- High current flows into a component(s) powered by VBAT (most likely the VHH power supply or an element powered by the VCC power supply).
- The voltage drop across the fuse will (prior to the fuse blowing) turn ON Q1 (based on the current flow through the fuse causing a 0.5V to 0.6V drop across the resistance of F1).
- The collector current from Q1 will turn off Q4.
- VBAT drops very quickly and, as a direct result, VCC falls. In turn, the voltage on the PortD4 IO pin from the microcontroller voltage falls as VCC falls, through the parasitic diodes in the microcontroller 24. This then pulls down the voltage across C6 as it is discharged through R12.
- The implantable pulse generator is now stable in the Dormant Mode, i.e., VBAT is disconnected from the battery 22 by a turned OFF Q4. The only load remaining on the battery is presented by the charging circuit and by the analog multiplexer (switches) U3 that are used to direct an analog voltage to the microcontroller 24 for monitoring the battery voltage and (by subtracting the voltage after the resistance of F1) an estimate of the current consumption of the entire circuit. A failure of these voltage monitoring circuits is not protected by the fuse, but resistance values limit the current flow to safe levels even in the event of component failures. A possible source of a transient high-current circuit failure is the SCR latchup or supply-to-ground short failure of a semiconductor device directly connected to VBAT or VCC.

i(a) (13) R9 & R11 form a voltage divider to convert VRAW (approximately zero volts to eight volts) into the voltage range of the microcontroller's A-D inputs (used for closed loop control of the RF magnetic field strength), i(a) (14) R8 and C9 form the usual R-C reset input circuit for the microcontroller 24; this circuit causes a hardware reset when the magnetic reed switch (S1) is closed by the application of a suitable static magnetic field for a short duration, i(a)(15) R10 and C8 form a much slower time constant that allows the closure of the reed switch by the application of the static magnetic field for a long duration to force the implantable pulse generator into the Dormant mode by turning OFF Q6 and thus turning OFF Q4. The use of the magnetic reed switch for resetting the microcontroller 24 or forcing a total implantable pulse generator shutdown (Dormant mode) may be a desirable safety feature.

ii. IPG Active Mode

The IPG Active mode occurs when the implantable pulse generator 18 is not being charged and it is operating normally. In this mode, the implantable pulse generator may be generating stimulus outputs or it may be waiting for the next request to generate stimulus in response to a timed neuromodulation sequence or a telemetry command from an external controller. In this mode, the implantable pulse generator is active (microcontroller 24 is powered and coordinating wireless communications and may be timing & controlling the generation and delivery of stimulus pulses). There is no implantable pulse generator charger 34 present.

ii(a) Principles of Operation, IPG Active Mode

In the IPG Active mode, there is no implantable pulse generator charger 34 present, and thus no DC voltage recovered by Receive Coil, D1, D2, and C3. In FIG. 11, the lack of DC current from VRAW means that Q5 is held off. This, in turn, holds Q3 off and the charging circuitry is isolated from the battery 22. In FIG. 12, the lack of DC current from VRAW means that U1 is disabled. This, in turn, keeps the current drain from the battery 22 to an acceptably low level, typically less than 1 μA.

iii. IPG Dormant Mode

The IPG Dormant mode occurs when the implantable pulse generator 18 is not being charged and it is completely disabled (powered down). In this mode, power is not being supplied to the microcontroller 24 or other enabled circuitry. This is the mode for the long-term storage of the implantable pulse generator before or after implantation. The dormant mode may only be exited by placing the implantable pulse generator into the Active and Charging mode by placing the implantable pulse generator charging coil 35 of a functional implantable pulse generator charger 34 in close proximity to the implantable pulse generator 18.

iii(a) Principles of Operation, IPG Dormant Mode

In the IPG Dormant mode, there is no implantable pulse generator charger 34 present, and thus no DC voltage recovered by Receive Coil, D1, D2, and C3. VBAT is not delivered to the remainder of the implantable pulse generator circuitry because Q4 is turned off. The Dormant mode is stable because the lack of VBAT means that VCC is also not present, and thus Q6 is not held on through R8 and R10. Thus the battery 22 is completely isolated from all load circuitry (the VCC power supply and the VHH power supply).

The Dormant mode is entered through the application of a long magnet placement over S1 (magnetic reed switch) or through the reception of a command by the wireless telemetry. In the case of the telemetry command, the PortD4, which is normally configured as a microcontroller input, is configured as a logic output with a logic low (0) value. This, in turn, discharges C8 through R12 and turns off Q6; which, in turn, turns off Q4 and forces the implantable pulse generator into the Dormant mode. Note that R12 is much smaller in value than R10, thus the microcontroller 24 can force C8 to discharge even though VCC is still present.

In FIG. 11, the lack of DC current from VRAW means that Q5 is held off. This, in turn, holds Q3 off and the charging circuitry is isolated from the battery 22. Also, Q4 was turned off. In FIG. 12, the lack of DC current from VRAW means that U1 is disabled. This, in turn, keeps the current drain from the battery 22 to an acceptably low level, typically less than 1 μA.

2. Representative Implantable Pulse Generator Circuitry

FIG. 6 shows a representative circuit 20 for the implantable pulse generator 18 that takes into account the desirable technical features discussed above.

The circuit 20 can be grouped into functional blocks, which generally correspond to the association and interconnection of the electronic components. FIG. 6 shows a block diagram that provides an overview of a representative desirable implantable pulse generator design.

In FIG. 6, seven functional blocks are shown: (1) The Microprocessor or Microcontroller 24; (2) the Power Management Circuit 40 for the battery 22; (3) the VCC Power Supply 42; (4) the VHH Power Supply 44; (5) the Stimulus Output Stage(s) 46; (6) the Output Multiplexer(s) 48; and (7) the Wireless Telemetry Circuit 50.

For each of these blocks, the associated functions, possible key components, and circuit description are now described.

a. The Microcontroller

The Microcontroller 24 is generally responsible for the following functions:

(1) The timing and sequencing of the stimulator stage and the VHH power supply used by the stimulator stage, (2) The sequencing and timing of power management functions, (3) The monitoring of the battery voltage, the voltage recovered from the RF magnetic field 52 during the battery charging process, the stimulator voltages produced during the generation of stimulus pulses, and the total circuit current consumption, VHH, and VCC, (4) The timing, control, and interpretation of commands to and from the wireless telemetry circuit, (5) The logging (recording) of patient usage data as well as clinician programmed stimulus parameters and configuration data, and (6) The processing of commands (data) received from the user (patient) via the wireless link to modify the characteristics of the stimulus being delivered.

The use of a microcontroller incorporating flash programmable memory allows the operating program of the implantable pulse generator as well as the stimulus parameters and settings to be stored in non-volatile memory (data remains safely stored even if the battery 22 becomes fully discharged, or if the implantable pulse generator is placed in the Dormant Mode). Yet, the data (operating program, stimulus parameters, usage history log, etc.) can be erased and reprogrammed thousands of times during the life of the implantable pulse generator. The software (firmware) of the implantable pulse generator must be segmented to support the operation of the wireless telemetry routines while the flash memory of the microcontroller 24 is being erased and reprogrammed. Similarly, the VCC power supply 42 must support the power requirements of the microcontroller 24 during the flash memory erase and program operations.

Although the microcontroller 24 may be a single component, the firmware is developed as a number of separate modules that deal with specific needs and hardware peripherals. The functions and routines of these software modules are executed sequentially; but the execution of these modules are timed and coordinated so as to effectively function simultaneously. The microcontroller operations that are associated directly with a given hardware functional block are described with that block.

The Components of the Microcontroller Circuit may include:

(1) A single chip microcontroller 24. This component may be a member of the Texas Instruments MSP430 family of flash programmable, micro-power, highly integrated mixed signal microcontroller. Likely family members to be used include the MSP430F1610, MSP430F1611, MSP430F1612, MSP430F168, and the MSP430F169. Each of these parts has numerous internal peripherals, and a micropower internal organization that allows unused peripherals to be configured by minimal power dissipation, and an instruction set that supports bursts of operation separated by intervals of sleep where the microcontroller suspends most functions.

(2) A miniature, quartz crystal (X1) for establishing precise timing of the microcontroller. This may be a 32.768 KHz quartz crystal.

(3) Miscellaneous power decoupling and analog signal filtering capacitors.

b. Power Management Circuit

The Power Management Circuit 40 (and associated microcontroller actions) is generally responsible for the following functions:

(1) recover power from the Receive Coil, (2) control delivery of the Receive Coil power to recharge the Lithium Ion secondary battery 22, (3) monitor the battery voltage during charge and discharge conditions, (4) communicate (through the wireless telemetry link 38) with the externally mounted implantable pulse generator charger 34 to increase or decrease the strength of the RF magnetic field 52 for optimal charging of the battery, (5) suspend stimulation when the battery voltage becomes very low, and/or suspend all operation (go into the Dormant Mode) when the battery voltage becomes critically low, (6) disable (with single fault tolerance) the delivery of charging current to the battery 22 in overcharge conditions, (7) communicate (through the wireless telemetry link 38) with the external equipment the charge status of the battery 22, (8) prevent (with single fault tolerance) the delivery of excessive current from the battery 22, (9) provide battery power to the rest of the circuitry of the implantable pulse generator, i.e., VCC and VHH power supplies,

(10) provide isolation of the Lithium Ion battery 22 from other circuitry while in the Dormant Mode,

(11) provide a hard microprocessor reset and force entry into the Dormant Mode in the presence of a pacemaker magnet (or comparable device), and

(12) provide the microcontroller 24 with analog voltages with which to measure the magnitude of the recovered power from the RF magnetic field 52, the battery voltage, and the appropriate battery current flow (drain and charge).

The Components of the Power Management Circuit may include:

(1) The Receive Coil, which desirably comprises a multi-turn, fine copper wire coil near the inside perimeter of the implantable pulse generator 18. Preferably, the receive coil includes a predetermined construction, e.g., desirably 250 to 350 turns, and more desirably 300 turns of four strands of #40 enameled magnetic wire, or the like. The maximizing of the coil's diameter and reduction of its effective RF resistance allows necessary power transfer at and beyond the typical implant depth of about one centimeter.

(2) A micropower Lithium Ion battery charge management controller IC (integrated circuit); such as the Micro-Chip MCP73843-41, or the like.

(3) Low on resistance, low threshold P channel MOSFETs with very low off state leakage current (Q2, Q3, and Q4).

(4) Analog switches (or an analog multiplexer) U3.

(5) Logic translation N-channel MOSFETs (Q5 & Q6) with very low off state leakage current.

c. The VCC Power Supply

The VCC Power Supply 42 is generally responsible for the following functions:

(1) Provide the microcontroller 24 and other circuitry with regulated 3.3 VDC (typical) despite changes in the Lithium Ion battery voltage. Other useable voltages include 3.0 VDC, 2.7 VDC, and the like.

The Components of the VCC Power Supply might include:

(1) Micropower, low drop out, linear voltage regulator; e.g., Microchip NCP1700T-3302, Maxim Semiconductor MAX1725, or Texas Instruments TPS79730, or the like.

The characteristics of the VCC Power Supply might include:

(1) quiescent current, i.e., the current wasted by the power supply in its normal operation. This value should be less than a few microamperes, and (2) drop-out voltage, i.e., the minimal difference between the VBAT supplied to the VCC power supply and its output voltage. This voltage may be less than about 100 mV even at the current loads presented by the transmitter of the wireless telemetry circuitry.

d. VHH Power Supply

Figure 13:
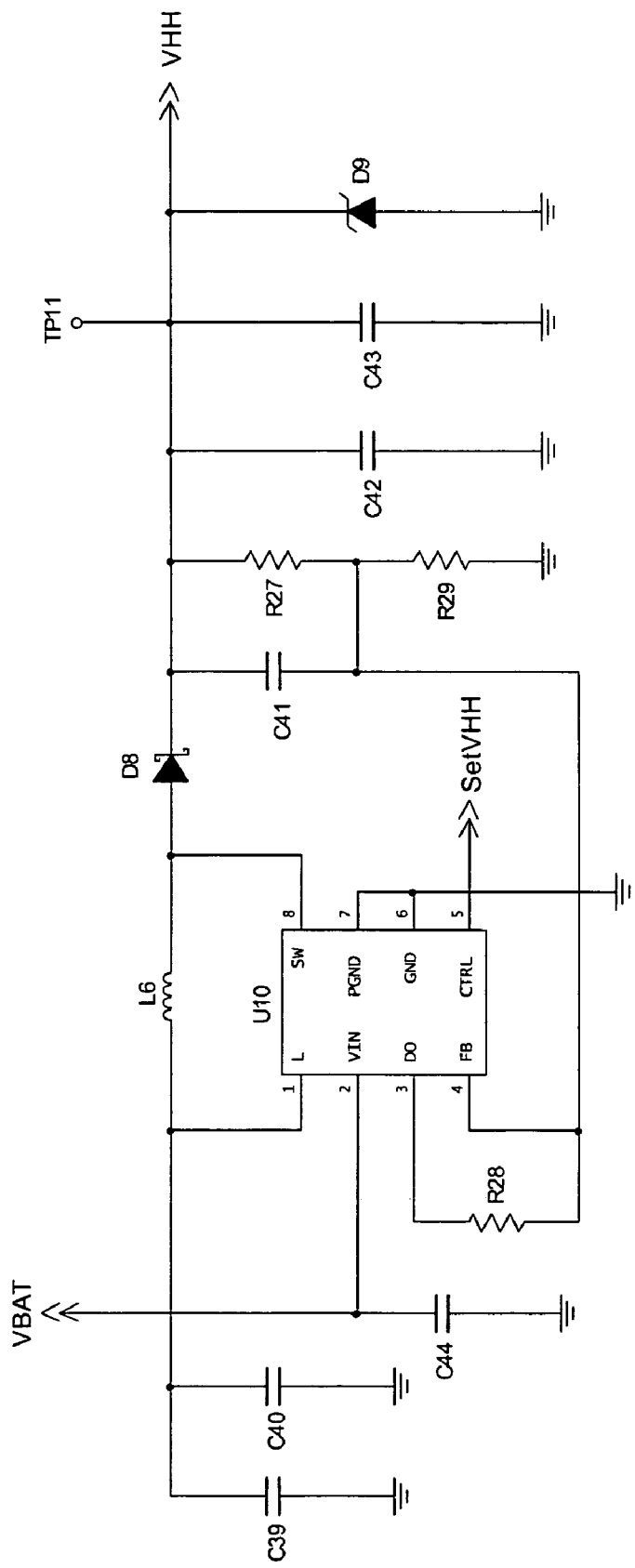
FIG. 13 is a circuit diagram showing a possible circuit for the VHH power supply feature used with the implantable pulse generator shown in FIGS. 2A and 2B.

A circuit diagram showing a desired configuration for the VHH power supply 44 is shown in FIG. 13. It is to be appreciated that modifications to this circuit diagram configuration which produce the same or similar functions as described are within the scope of the invention.

The VHH Power Supply 44 is generally responsible for the following functions:

(1) Provide the Stimulus Output Stage 46 and the Output Multiplexer 48 with a programmable DC voltage between the battery voltage and a voltage high enough to drive the required cathodic phase current through the electrode circuit plus the voltage drops across the stimulator stage, the output multiplexer stage, and the output coupling capacitor. VHH is typically 12 VDC or less for neuromodulation applications; and 25V or less for muscle stimulation applications.

The Components of the VHH Power Supply might include:

(1) Micropower, inductor based (fly-back topology) switch mode power supply (U10); e.g., Texas Instruments TPS61045, Texas Instruments TPS61041, or Linear Technology LT3464 with external voltage adjustment components.

(2) L6 is the flyback energy storage inductor.

(3) C42 & C43 form the output capacitor.

(4) R27, R28, and R29 establish the operating voltage range for VHH given the internal DAC which is programmed via the SETVHH logic command from the microcontroller 24.

(5) Diode D9 serves no purpose in normal operation and is added to offer protection from over-voltage in the event of a VHH circuit failure.

(6) The microcontroller 24 monitors VHH for detection of a VHH power supply failure, system failures, and optimizing VHH for the exhibited electrode circuit impedance.

e. Stimulus Output Stage

The Stimulus Output Stage(s) 46 is generally responsible for the following functions:

(1) Generate the identified biphasic stimulus current with programmable (dynamically adjustable during use) cathodic phase amplitude, pulse width, and frequency. The recovery phase may incorporate a maximum current limit; and there may be a delay time (most likely a fixed delay) between the cathodic phase and the recovery phase (see FIG. 9). Typical currents (cathodic phase) for neuromodulation applications are 1 mA to 10 mA; and 2 mA to 20 mA for muscle stimulation applications. For applications using nerve cuff electrodes or other electrodes that are in very close proximity to the excitable neural tissue, stimulus amplitudes of less than 1 mA may be provided. Electrode circuit impedances can vary with the electrode and the application, but are likely to be less than 2,000 ohms and greater than 100 ohms across a range of electrode types.

The Components of the Stimulus Output Stage (as represented in FIG. 8) may include:

(1) The cathodic phase current through the electrode circuit is established by a high gain (HFE) NPN transistor (Q7) with emitter degeneration. In this configuration, the collector current of the transistor (Q7) is defined by the base drive voltage and the value of the emitter resistor (R24).

Two separate configurations are possible: In the first configuration (as shown in FIG. 8), the base drive voltage is provided by a DAC peripheral inside the microcontroller 24 and is switched on and off by a timer peripheral inside the microcontroller. This switching function is performed by an analog switch (U8). In this configuration, the emitter resistor (R24) is fixed in value and fixed to ground.

In a second alternative configuration, the base drive voltage is a fixed voltage pulse (e.g., a logic level pulse) and the emitter resistor is manipulated under microcontroller control. Typical options may include resistor(s) terminated by microcontroller IO port pins that are held or pulsed low, high, or floating; or an external MOSFET that pulls one or more resistors from the emitter to ground under program control. Note that the pulse timing need only be applied to the base drive logic; the timing of the emitter resistor manipulation is not critical.

The transistor (Q7) desirably is suitable for operation with VHH on the collector. The cathodic phase current through the electrode circuit is established by the voltage drop across the emitter resistor. Diode D7, if used, provides a degree of temperature compensation to this circuit.

(2) The microcontroller 24 (preferably including a programmable counter/timer peripheral) generates stimulus pulse timing to generate the cathodic and recovery phases and the interphase delay. The microcontroller 24 also monitors the cathode voltage to confirm the correct operation of the output coupling capacitor, to detect system failures, and to optimize VHH for the exhibited electrode circuit impedance; i.e., to measure the electrode circuit impedance. Additionally, the microcontroller 24 can also monitor the pulsing voltage on the emitter resistor; this allows the fine adjustment of low stimulus currents (cathodic phase amplitude) through changes to the DAC value.

f. The Output Multiplexer

The Output Multiplexer 48 is generally responsible for the following functions:

(1) Route the Anode and Cathode connections of the Stimulus Output Stage 46 to the appropriate electrode based on addressing data provided by the microcontroller 24.

(2) Allow recharge (recovery phase) current to flow from the output coupling capacitor back through the electrode circuit with a programmable delay between the end of the cathodic phase and the beginning of the recovery phase (the interphase delay).

The circuit shown in FIG. 8 may be configured to provide monopolar stimulation (using the case 26 as the return electrode) to Electrode 1, to Electrode 2, or to both through time multiplexing. This circuit could also be configured as a single bipolar output channel by changing the hardwire connection between the circuit board and the electrode; i.e., by routing the CASE connection to Electrode 1 or Electrode 2. The use of four or more channels per multiplexer stage (i.e., per output coupling capacitor) is likely.

The Components of the Output Multiplexer might include:

(1) An output coupling capacitor in series with the electrode circuit. This capacitor is desirably located such that there is no DC across the capacitor in steady state. This capacitor is typically charged by the current flow during the cathodic phase to a voltage range of about ¼th to ⅒th of the voltage across the electrode circuit during the cathodic phase. Similarly, this capacitor is desirably located in the circuit such that the analog switches do not experience voltages beyond their ground of power supply (VHH).

(2) The analog switches (U7) must have a suitably high operating voltage, low ON resistance, and very low quiescent current consumption while being driven from the specified logic levels. Suitable analog switches include the Vishay/Siliconix DG412HS, for example.

(3) Microcontroller 24 selects the electrode connections to carry the stimulus current (and time the interphase delay) via address lines.

(4) Other analog switches (U9) may be used to sample the voltage of VHH, the CASE, and the selected Electrode. The switched voltage, after the voltage divider formed by R25 and R26, is monitored by the microcontroller 24.

g. Wireless Telemetry Circuit

The Wireless Telemetry circuit 50 is generally responsible for the following functions:

(1) Provide reliable, bidirectional communications (half duplex) with an external controller, programmer, or charger 34, for example, via a VHF-UHF RF link (likely in the 403 MHZ to 406 MHz MICS band per FCC 47 CFR Part 95 and the Ultra Low Power—Active Medical Implant (AMI) regulations of the European Union). This circuit will look for RF commands at precisely timed intervals (e.g., twice a second), and this function must consume very little power. Much less frequently this circuit will transmit to the external controller. This function should also be as low power as possible; but will represent a lower total energy demand than the receiver in most of the anticipated applications. The RF carrier is amplitude modulated (on-off keyed) with the digital data. Serial data is generated by the microcontroller 24 already formatted and timed. The wireless telemetry circuit 50 converts the serial data stream into a pulsing carrier signal during the transit process; and it converts a varying RF signal strength into a serial data stream during the receive process.

The Components of the Wireless Telemetry Circuit (as represented in FIG. 7) might include:

(1) a crystal controlled, micropower transceiver chip such as the AMI Semiconductor AMIS-52100 (U6). This chip is responsible for generating the RF carrier during transmissions and for amplifying, receiving, and detecting (converting to a logic level) the received RF signals. The transceiver chip must also be capable of quickly starting and stopping operation to minimize power consumption by keeping the chip disabled (and consuming very little power) the majority of the time; and powering up for only as long as required for the transmitting or receiving purpose.

(2) The transceiver chip has separate transmit and receive ports that must be switched to a single antenna/feedthru. This function is performed by the transmit/receive switch (U5) under microcontroller control via the logic line XMIT. The microcontroller 24 controls the operation of the transceiver chip via an I²C serial communications link. The serial data to and from the transceiver chip may be handled by a UART or a SPI peripheral of the microcontroller. The message encoding/decoding and error detection may be performed by a separate, dedicated microcontroller; else this processing will be time shared with the other tasks of the only microcontroller.

The various inductor and capacitor components (U6) surrounding the transceiver chip and the transmit/receive switch (U5) are impedance matching components and harmonic filtering components, except as follows:

(1) X2, C33 and C34 are used to generate the crystal controlled carrier, desirably tuned to the carrier frequency divided by thirty-two, (2) L4 and C27 form the tuned elements of a VCO (voltage controlled oscillator) operating at twice the carrier frequency, and (3) R20, C29, and C30 are filter components of the PLL (phase locked loop) filter.

II. Representative Indications

Due to its technical features, the implantable pulse generator 18 as just generally described can be used to provide beneficial results in diverse therapeutic and functional restorations indications.

For example, in the field of urology, possible indications for use of the implantable pulse generator 18 include the treatment of (i) urinary and fecal incontinence; (ii) micturition/retention; (iii) restoration of sexual function; (iv) defecation/constipation; (v) pelvic floor muscle activity; and/or (vi) pelvic pain.

The implantable pulse generator 18 can be used for deep brain stimulation in the treatment of (i) Parkinson's disease; (ii) multiple sclerosis; (iii) essential tremor; (iv) depression; (v) eating disorders; (vi) epilepsy; and/or (vii) minimally conscious state.

The implantable pulse generator 18 can be used for pain management by interfering with or blocking pain signals from reaching the brain, in the treatment of, e.g., (i) peripheral neuropathy; and/or (ii) cancer.

The implantable pulse generator 18 can be used for vagal nerve stimulation for control of epilepsy, depression, or other mood/psychiatric disorders.

The implantable pulse generator 18 can be used for the treatment of obstructive sleep apnea.

The implantable pulse generator 18 can be used for gastric stimulation to prevent reflux or to reduce appetite or food consumption.

The implantable pulse generator 18 can be used in functional restorations indications such as the restoration of motor control, to restore (i) impaired gait after stroke or spinal cord injury (SCI); (ii) impaired hand and arm function after stroke or SCI; (iii) respiratory disorders; (iv) swallowing disorders; (v) sleep apnea; and/or (vi) neurotherapeutics, allowing individuals with neurological deficits, such as stroke survivors or those with multiple sclerosis, to recover functionally.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:
1. A neuromuscular stimulation system comprising:
at least one electrically conductive surface sized and configured for implantation in a targeted neural or muscular tissue region affecting urologic function,
a lead electrically coupled to the electrically conductive surface, the lead sized and configured to be positioned subcutaneous a tissue surface,
an implantable pulse generator sized and configured to be coupled to the lead and positioned subcutaneous to a tissue surface in an anterior pelvic region remote from the at least one electrically conductive surface, the implantable pulse generator comprising a case having a size between about 5 mm and about 10 mm thick, between about 15 mm and about 40 mm, and between about 40 mm and about 60 mm long, and the implantable pulse generator comprising non-inductive wireless telemetry circuitry using VHF/UHF signals, the non-inductive wireless telemetry circuitry being functional at a distance as far as arm's reach away from the patient, and being adapted for programming and interrogation of the implantable pulse generator.

2. A system according to claim 1
wherein the implantable pulse generator is sized and configured for implanting in subcutaneous tissue at an implant depth of between about 0.5 cm and about 1.5 cm.

3. A system according to claim 1
further including a rechargeable battery carried within the case, the rechargeable battery having a capacity of at least 30 mA-hr.

4. A system according to claim 1
further including a rechargeable battery carried within the case, the rechargeable battery having a capacity of at least 30 mA-hr, and the implantable pulse generator being sized and configured for implanting in subcutaneous tissue at an implant depth of between about 0.5 cm and about 1.5 cm.

5. A neuromuscular stimulation system comprising:
at least one electrically conductive surface sized and configured for implantation in a targeted neural or muscular tissue region affecting urologic function,
a lead electrically coupled to the electrically conductive surface, the lead sized and configured to be positioned subcutaneous a tissue surface,
an implantable pulse generator comprising a case sized and configured to be coupled to the lead and positioned subcutaneous to a tissue surface in an anterior pelvic region remote from the at least one electrically conductive surface, the implantable pulse generator being sized and configured for implanting in subcutaneous tissue at an implant depth of between about 0.5 cm and about 1.5 cm, and the implantable pulse generator comprising non-inductive wireless telemetry circuitry using VHF/UHF signals, the non-inductive wireless telemetry circuitry being functional at a distance as far as arm's reach away from the patient, and being adapted for programming and interrogation of the implantable pulse generator.

6. A system according to claim 5
further including a rechargeable battery carried within the case, the rechargeable battery having a capacity of at least 30 mA-hr.

7. A neuromuscular stimulation system comprising:
at least one electrically conductive surface sized and configured for implantation in a targeted neural or muscular tissue region affecting urologic function, a lead electrically coupled to the electrically conductive surface, the lead sized and configured to be positioned subcutaneous a tissue surface, an implantable pulse generator sized and configured to be coupled to the lead and positioned subcutaneous to a tissue surface in an anterior pelvic region remote from the at least one electrically conductive surface, the implantable pulse generator comprising a generally pear-shaped case having a size between about 5 mm and about 10 mm thick, between about 15 mm and about 40mm wide, and between about 40 mm and about 60 mm long, pulse generation circuitry carried within the case, and a rechargeable battery coupled to the circuitry and carried within the case, the battery having a capacity of at least 30 mA-hr.

8. A system according to claim 1 or 5 or 7
wherein the urologic function is selected from the group consisting of urinary incontinence, fecal incontinence, micturition/retention, defecation/constipation, restoration of sexual function, pelvic floor muscle activity, and pelvic pain.

9. A system according to claim 1 or 5 or 7
wherein the case includes a smaller end and a larger end to facilitate placement within a subcutaneous pocket small end first.

10. A system according to claim 1 or 5 or 7
wherein the case includes a connection header coupled to the circuitry, the connection header being sized and configured to accept an IS-1 plug-in lead connector.

11. A system according to claim 7
further including a power receiving coil coupled to the rechargeable battery and carried entirely within the case, the power receiving coil being configured, after the case is implanted in subcutaneous tissue, to transfer received power from a transcutaneously applied radio frequency magnetic field to the rechargeable battery and recharge the battery in a time period of not more than six hours.

12. A system according to claim 7
wherein recharging of the rechargeable battery is required less than weekly.

13. A system according to claim 7
wherein the implantable pulse generator is sized and configured for implanting in subcutaneous tissue at an implant depth of between about 0.5 cm and about 1.5 cm.

14. A system according to claim 7 or 3 or 6
wherein the rechargeable battery has a capacity at or about 35 mA-hr.

15. A method comprising
providing at least one electrically conductive surface sized and configured for implantation in a targeted neural or muscular tissue region affecting urologic function, the at least one electrically conductive surface including a lead electrically coupled to the electrically conductive surface, the lead sized and configured to be positioned subcutaneous a tissue surface,
providing an implantable pulse generator sized and configured to be positioned subcutaneous to a tissue surface in an anterior pelvic region remote from the at least one electrically conductive surface, the implantable pulse generator comprising a case having a size between about 5 mm and about 10 mm thick, between about 15 mm and about 40 mm wide, and between about 40 mm and about 60 mm long, and the implantable pulse generator comprising non-inductive wireless telemetry circuitry using VHF/UHF signals, the non-inductive wireless telemetry circuitry being functional at a distance as far as arm's reach away from the patient, and being adapted for programming and interrogation of the implantable pulse generator,
implanting the at least one electrically conductive surface in a targeted neural or muscular tissue region affecting urologic function,
implanting the lead in subcutaneous tissue,
implanting the pulse generator in an anterior pelvic region remote from the at least one electrically conductive surface,
coupling the pulse generator to the lead implanted in subcutaneous tissue, and
operating the pulse generator to apply neuromuscular stimulation pulses to the at least one electrically conductive surface to treat the urologic function.

16. A method according to claim 15
further including programming and/or interrogating the implantable pulse generator using the non-inductive wireless telemetry circuitry.

17. A method comprising
providing at least one electrically conductive surface sized and configured for implantation in a targeted neural or muscular tissue region affecting urologic function, the at least one electrically conductive surface including a lead electrically coupled to the at least one electrically conductive surface, the lead sized and configured to be positioned subcutaneous a tissue surface,
providing an implantable pulse generator comprising a case sized and configured to be positioned subcutaneous to a tissue surface in an anterior pelvic region remote from the at least one electrically conductive surface, the implantable pulse generator being sized and configured for implanting in subcutaneous tissue at an implant depth of between about 0.5 cm and about 1.5 cm, and the implantable pulse generator comprising non-inductive wireless telemetry circuitry using VHF/UHF signals, the non-inductive wireless telemetry circuitry being functional at a distance as far as arm's reach away from the patient, and being adapted for programming and interrogation of the implantable pulse generator,
implanting the at least one electrically conductive surface in a targeted neural or muscular tissue region affecting urologic function,
implanting the lead in subcutaneous tissue,
implanting the pulse generator in an anterior pelvic region remote from the at least one electrically conductive surface, and at an implant depth of between about 0.5 cm and about 1.5 cm,
coupling the pulse generator to the lead implanted in subcutaneous tissue, and
operating the pulse generator to apply neuromuscular stimulation pulses to the at least one electrically conductive surface to treat the urologic function.

18. A method according to claim 17
further including programming and/or interrogating the implantable pulse generator using the non-inductive wireless telemetry circuitry.

19. A method comprising
providing at least one electrically conductive surface sized and configured for implantation in a targeted neural or muscular tissue region affecting urologic function, the at least one electrically conductive surface including a lead electrically coupled to the at least one electrically conductive surface, the lead sized and configured to be positioned subcutaneous a tissue surface, providing an implantable pulse generator sized and configured to be positioned subcutaneous to a tissue surface in an anterior pelvic region remote from the at least one electrically conductive surface, the implantable pulse generator comprising a generally pear-shaped case having a size between about 5 mm and about 10 mm thick, between about 15 mm and about 40 mm wide, and between about 40 mm and about 60 mm long, pulse generation circuitry carried within the case, and a rechargeable battery coupled to the circuitry and carried within the case, the battery having a capacity of at least 30 mA-hr, implanting the at least one electrically conductive surface in a targeted neural or muscular tissue region affecting urologic function, implanting the lead in subcutaneous tissue, implanting the pulse generator in an anterior pelvic region remote from the at least one electrically conductive surface, coupling the pulse generator to the lead implanted in subcutaneous tissue, and operating the pulse generator to apply neuromuscular stimulation pulses to the at least one electrically conductive surface to treat the urologic function.

20. A method according to claim 19 wherein implanting includes inserting the implantable pulse generator in a subcutaneous pocket with the smaller end being pushed in first and the larger end being pushed in last.

21. A method according to claim 15 or 17 or 19 wherein the urologic function is selected from the group consisting of urinary incontinence, fecal incontinence, mictarition/retention, defecation/constipation, restoration of sexual function, pelvic floor muscle activity, and pelvic pain.

22. A method according to claim 19 wherein the rechargeable battery has a capacity at or about 35 mA-hr.

* * * * *